United States Patent [19]
Furlan et al.

[11] Patent Number: 6,068,838
[45] Date of Patent: May 30, 2000

[54] PURIFIED MULTIMERASE

[75] Inventors: Miha Furlan, Bern; Bernhard Laemmle, Bollingen, both of Switzerland; Hans Peter Schwarz, Vienna, Austria; Peter Turecek, Klosterneuburg Weidling, Austria; Johann Eibl, Vienna, Austria

[73] Assignee: Baxter Aktiengesellschaft, Vienna, Austria

[21] Appl. No.: 08/656,589

[22] Filed: May 31, 1996

[30] Foreign Application Priority Data

Apr. 29, 1996 [AT] Austria ..................... 769/96
Apr. 29, 1996 [AT] Austria ..................... 770/96

[51] Int. Cl.⁷ .............. A61K 38/48; A61K 38/46; C12N 9/48; C12N 9/50
[52] U.S. Cl. ................. 424/94.63; 424/94.67; 435/212; 435/217; 435/814
[58] Field of Search ............. 424/94.63, 94.67; 435/212, 217, 814

[56] References Cited

FOREIGN PATENT DOCUMENTS

| | | |
|---|---|---|
| 0131740A2 | 1/1985 | European Pat. Off. . |
| 0159311A1 | 10/1985 | European Pat. Off. . |
| 0197592A1 | 10/1986 | European Pat. Off. . |
| 0197592B1 | 10/1986 | European Pat. Off. . |
| 0353218A3 | 1/1990 | European Pat. Off. . |
| 0503991A1 | 9/1992 | European Pat. Off. . |
| 0519901A2 | 12/1992 | European Pat. Off. . |
| 4434538A1 | 4/1995 | European Pat. Off. . |
| 4435485C1 | 3/1996 | Germany . |
| WO94/13329 | 6/1994 | WIPO . |
| WO96/10584 | 4/1996 | WIPO . |

OTHER PUBLICATIONS

M. Aihara et al., Thrombosis & Haemostatis, 55(2(: 263–267 (1986).
Z. Ruggeri et al., Blood, 57(6): 1140–1143 (Jun. 1981).
U.K. Laemli, Nature, 227: 680–685 (Aug. 15, 1970).
M. Furlan et al., Proc. Natl. Acad. Sci. USA, 90: 7503–7507 (Aug. 1993).
B. Fischer et al., FEBS Letters, 375: 259–262 (1995).
Furlan et al. Blood 87(10): 4223–4234, May 15, 1996.
Tsai Blood 87(10):4235–4244, May 15, 1996.
Kunicki et al. Blood 2: 352–356 (Feb. 1985).
Dent et al. Proc. Natl. Acad. Sci. USA 87: 6306–6310 (Aug. 1990).
Berkowitz et al. Blood 72(5): 1790–1796 (Nov. 1988).
Furlan et al. Blod 87(10): 4223–4234 (May 1996).
Furlan et al. Thombosis Research vol. 10: 153–158, 1977.
Furlan et al. PNAS 90: 7503–7507, 1993.

*Primary Examiner*—Chris Eisenchenk
*Assistant Examiner*—Mary K Zeman
*Attorney, Agent, or Firm*—Foley & Lardner

[57] ABSTRACT

There is disclosed a purified multimerase having an indirect and a direct proteolytic activity, which converts vWF having a singlet structure to vWF having a satellite structure and is active in the presence of the serine protease inhibitor DFP or the calpain protease inhibitor Z-Leu-Leu-Tyr-CHN$_2$, as well as a method of preparing the multimerase according to the invention.

32 Claims, 18 Drawing Sheets

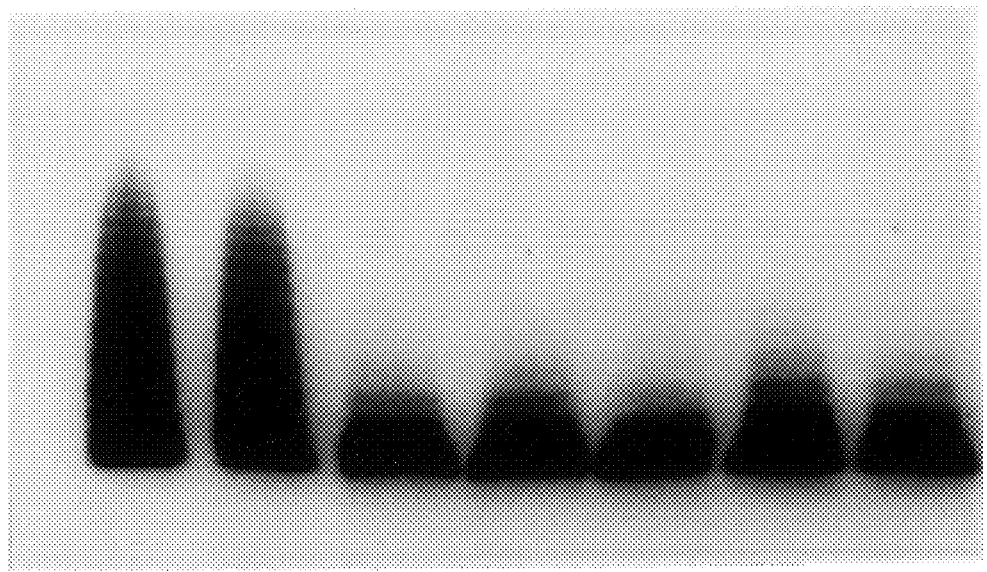

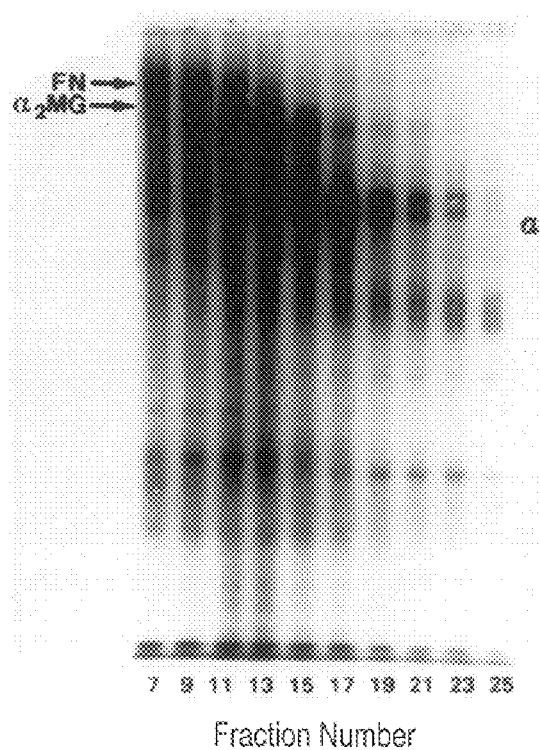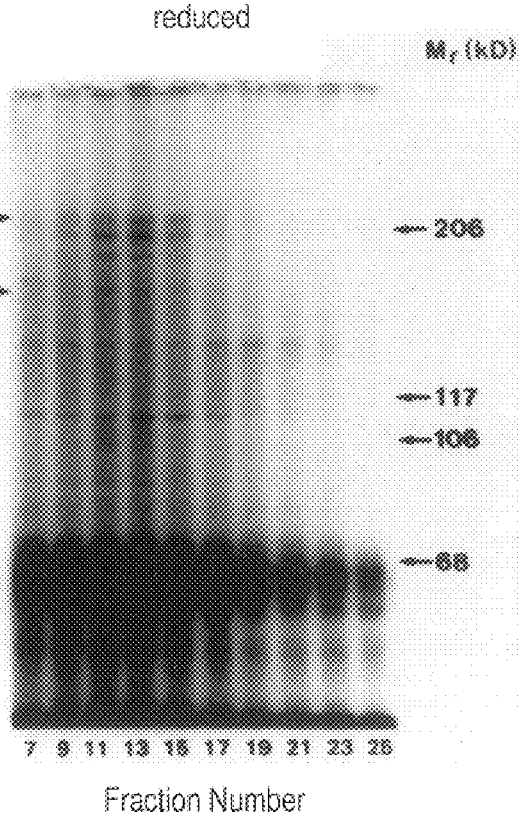
FIG. 7A unreduced
FIG. 7B reduced

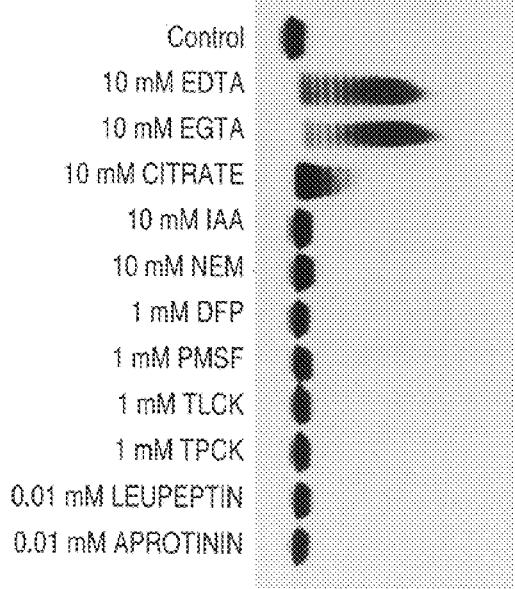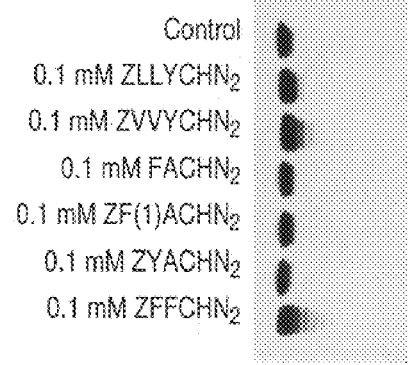

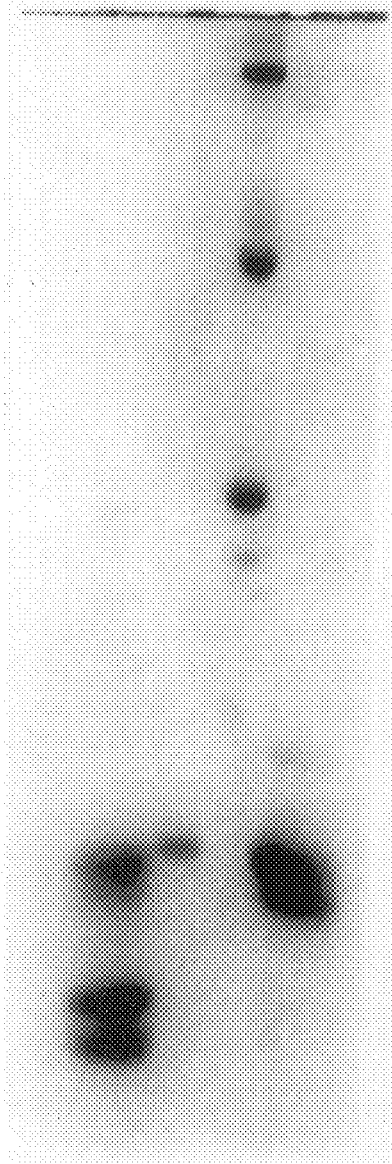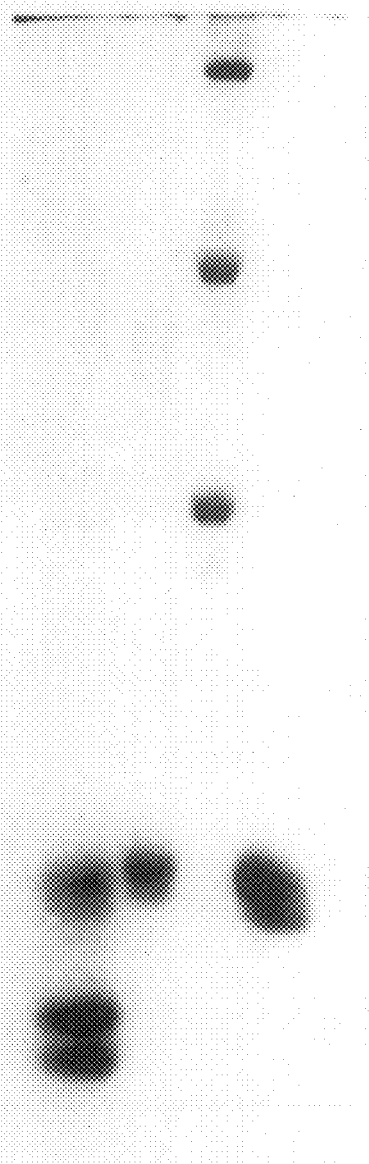
FIG. 11A — 24h 37° C — Kontrolle
FIG. 11B — 24h 37° C — + Protease

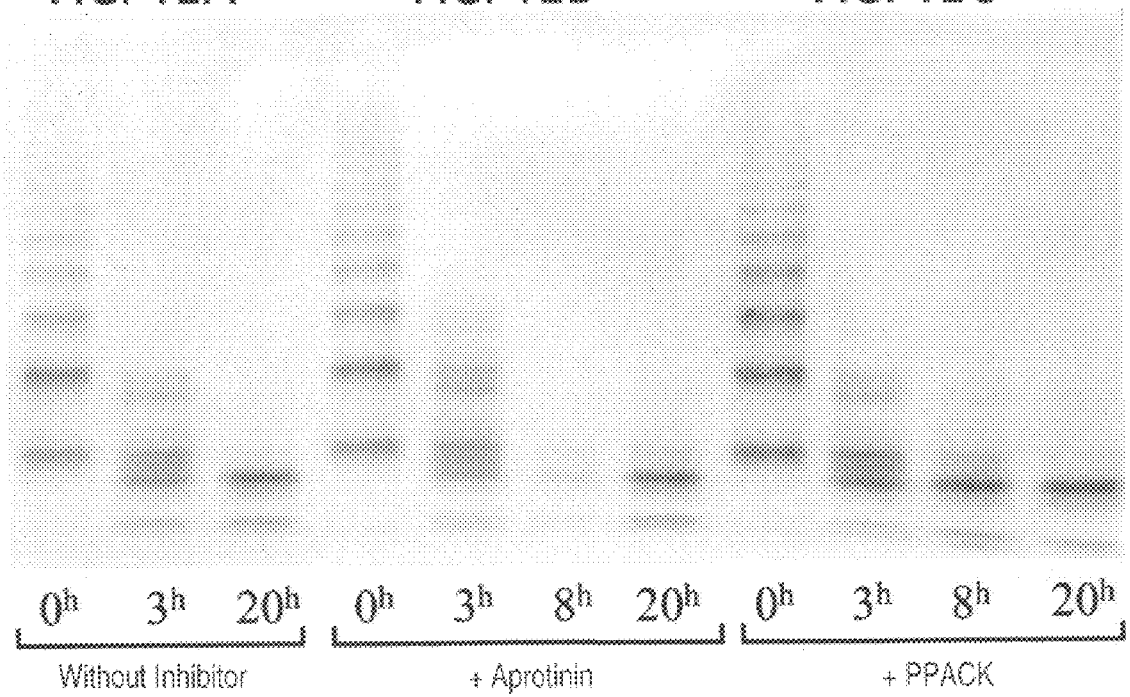

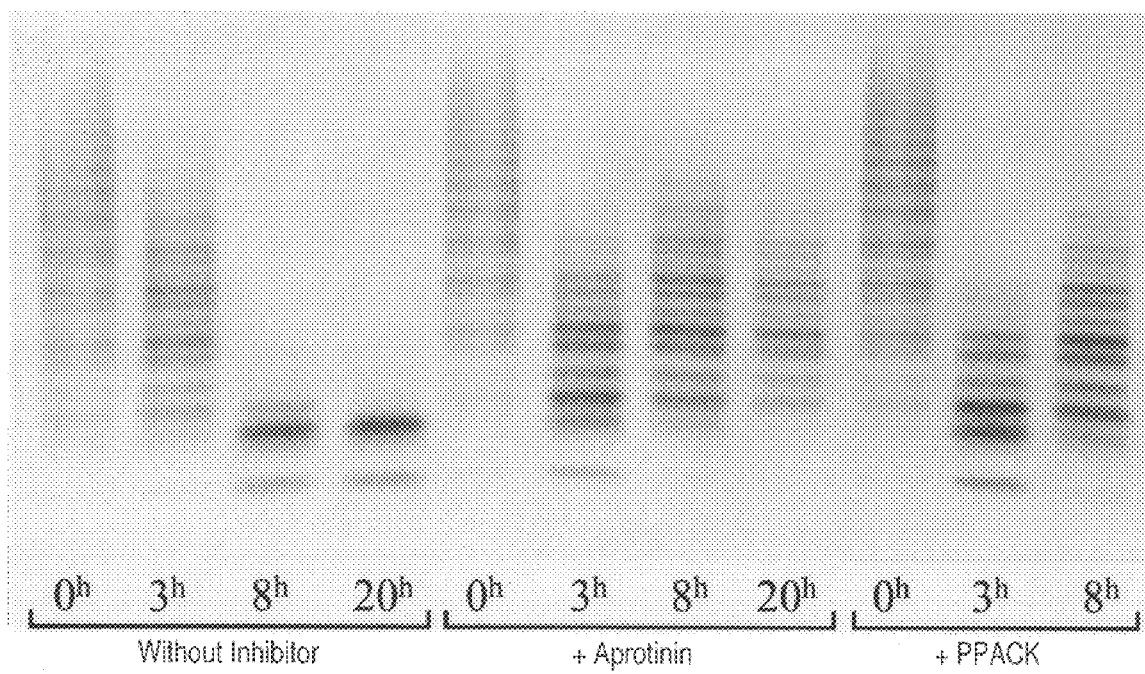

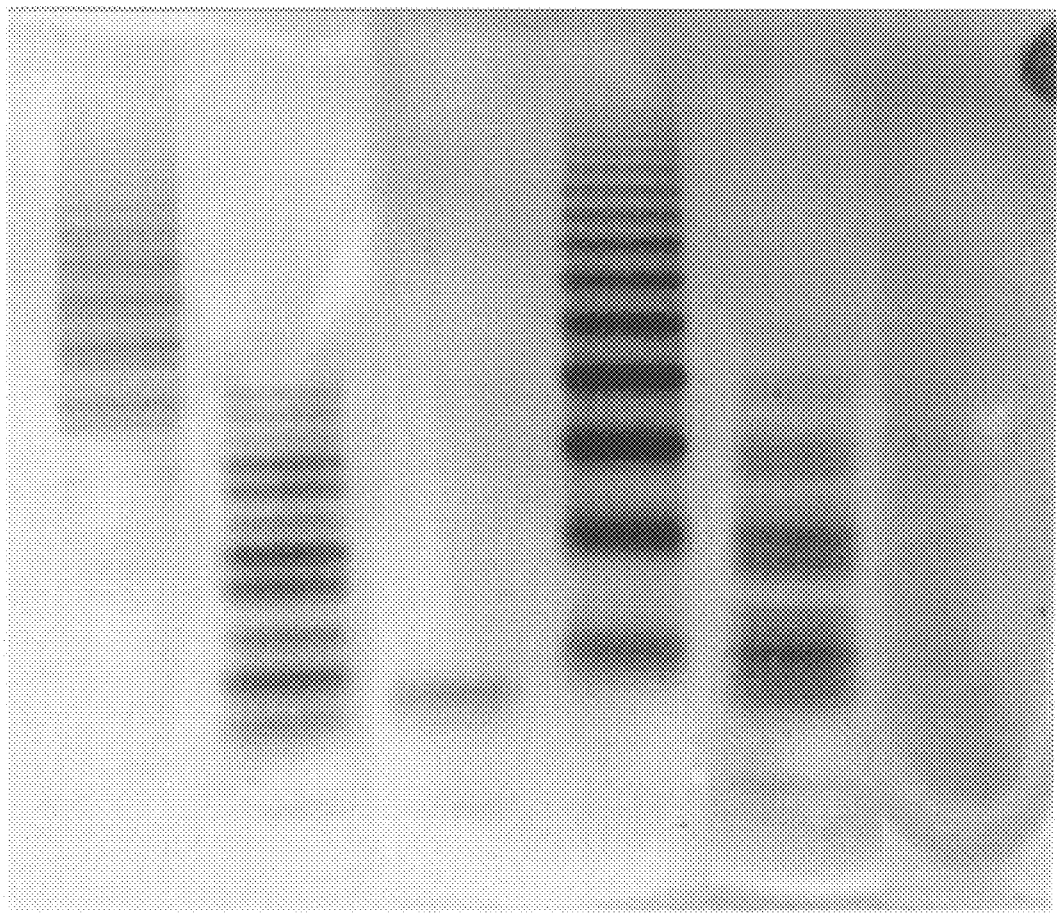
FIG. 14A vWF-High Multimers
FIG. 14B after "vW-Multimerase"
FIG. 14C rvWF
FIG. 14D after "vW-Multimerase" after Plasmin

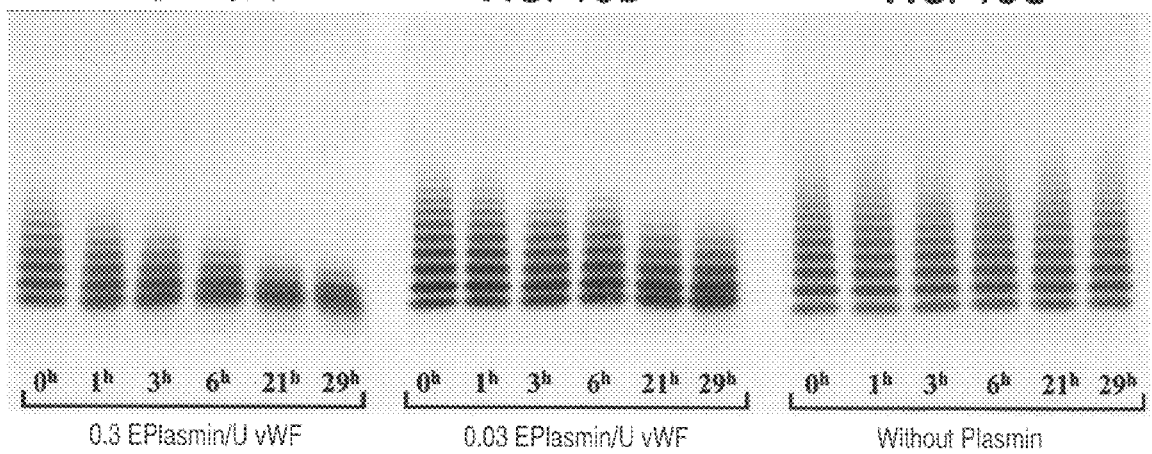

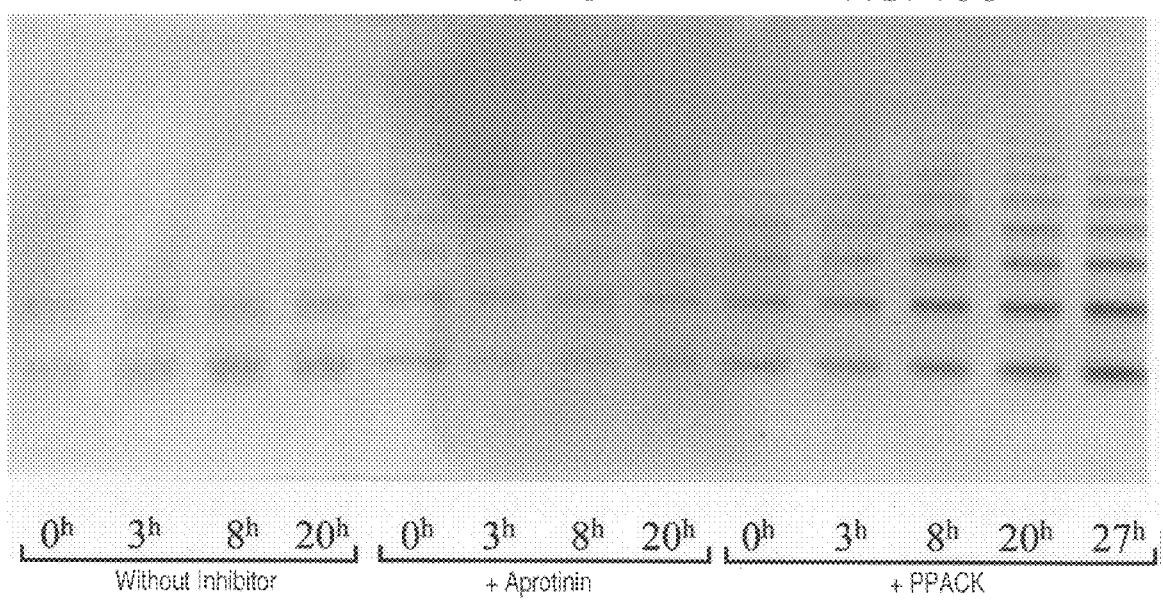

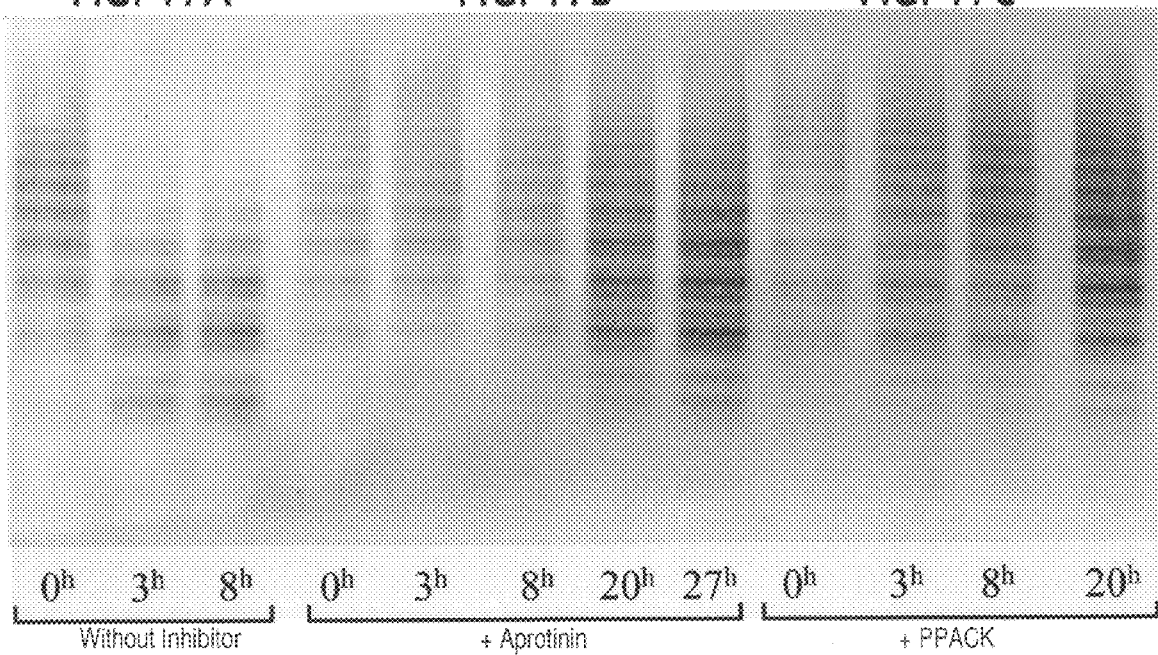

PURIFIED MULTIMERASE

The invention relates to a preparation comprising von Willebrand factor protease, a method of preparing the same as well as a method of preparing von Willebrand factor with satellite structure.

Von Willebrand factor (vWF) in a glycoprotein circulating in plasma as a series of multimers ranging in size from about 500 to 20,000 kD. Multimeric forms of vWF are composed of 250 kD polypeptide subunits linked together by disulfide bonds. vWF mediates the initial platelet adhesion to the subendothelium of the damaged vessel wall, only the larges multimers also exhibiting a haemostatic activity. It is assumed that endothelial cells secrete large polymeric forms of vWF and that those forms of vWF which have a low molecular weight (low molecular weight vWF, LMW) have arisen from proteolytic cleavage.

The multimers having large molecular masses are stored in the Weibel Palade bodies of the endothelial cells and are liberated upon stimulation.

vWF can bind blood coagulation factor VIII, thus forming the factor VIII complex or factor VIII:C/vWF complex which contains factor VIII:C as a stabilized protein. A vWF deficiency necessarily also will lead to a reduction in the factor VIII:C concentration in blood, since the stabilizing effect of vWF is missing.

The proteolytic degradation of vWF is a physiological process in healthy individuals, yet in patients suffering from von Willebrand disease (vWD) type 2A it may be accelerated, and as a consequence these patients lack the vWF multimers with the largest molecular masses.

A small portion of the vWF present in normal plasma circulates as 189, 176 and 140 kD fragments resulting from proteolytic degradation of vWF in vivo, the 140 kD fragment being derived from the N-terminal region, and the 176 kD fragment from the C-terminal region of the subunit. LMW forms of vWF were isolated from normal human plasma and subjected to SDS-PACE after disulfide reduction. The unusually high portion of vWF fragments is compatible with the view that the LMW forms of vWF have been partially or predominantly derived from large multimers by proteolytic degradation.

The infusion of 1-desamino-8-D-arginine vasopressin in normal subjects was followed by the appearance in plasma of multimers of large molecular masses that were subsequently rapidly cleaved through proteolytic degradation. A lack of large vWF multimers and an increased level of proteolytic fragments were also observed in acquired von Willebrand disease (vWD) associated with myeloproliferative syndrome, indicating increased in vivo proteolysis in this condition as well. Unusually large molecular forms of vWF were found in patients with thrombotic thrombocytopenic purpura (TTP); these large multimers disappeared after transfusion with normal fresh frozen plasma. It is evident that proteolytic enzyme(s) are involved in the physiological regulation of the polymeric size of vWF in the circulating blood and that they also play an important role in the pathogenesis of vWF abnormalities in some patients with congenital or acquired disorders of hemostasis; however, the proteolytic enzyme responsible for vWF proteolysis in normal human plasma has not yet been identified.

Several proteases have been shown to be able to cleave vWF, thereby impairing its binding affinity for platelets; however, treatment of vWF with these proteases in each case resulted in cleavage products different from the fragments derived from in vivo cleavage.

Thus, e.g., plasmin is capable of cleaving several peptide bonds in vWF, yet there remains a high molecular weight core region retaining about 70% of the platelet agglutinating activity (determined as ristocetin cofactor). A 34 kD peptide was split from the N-termini of individual vWF subunits in the early stage of the treatment with plasmin. Epitope mapping of plasmin-induced fragments clearly showed that these fragments originated from regions of the vWF subunit that were different from the fragments present in circulating plasma.

Porcine pancreatic elastase and various serine proteases released from human leukocytes were shown to degrade vWF proteolytically with a resultant loss of large multimers. Epitope mapping of the degradation products again indicated that these fragments also differed from those present in normal plasma and in vWD type 2A. Moreover, vWF multimeric patterns in plasma samples from patients with extremely high or low neutrophil counts were not significantly different from those in normal human plasma.

In addition to the above serine proteases, a calpain-like protease released from human platelets was also shown to degrade large vWF multimers.

Furthermore, analysis of the circulating vWF fragments indicated that the peptide bond between amino acid residues 842Tyr and 843Met is cleaved in the vWF subunit of patients with vWD of type 2A: a cleavage site indicating a calpain-like specificity. However, it could also be shown that calpains from porcine erythrocytea and porcine kidney in vivo failed to generate the vWF fragments produced.

Recombinant vWF (r-vWF) can be produced in CHO cells, e.g. according to FEBS Letter 375, 259–262 (1995). The r-vWF recovered in this manner is available as a mature vWF and has a singlet structure, i.e. it differs from plasmatic vWF, which always has a characteristic satellite structure when examined on 2% SDS agarose gels.

In WO 96/10584 it is described that the r-vWF is comprised of multimers with high structural integrity which is retained even after purification and treatment for the inactivation of viruses. The intact structure of the r-vWF is defined by a result of electrophoretic analysis consisting of multimer bands with an absence of satellite bands.

To prepare an r-vWF preparation having a structure corresponding to that of plasmatic vWF from the r-vWF with singlet structure, a treatment with a physiological vWF protease activity is thus necessary.

Thus it is the object of the present invention to provide an enzyme activity which is capable of proteolytically processing vWF in a physiologic manner and optionally to degrade the same, and, respectively, to provide a preparation which comprises such an enzyme activity.

Since the pathologic symptoms due to abnormal vWF degrading activities or due to an increased vWF level may often cause thromboses or thromboembolic disorders, it is a further object of the present invention to re-adjust the normal levels by a pharmaceutical preparation comprising a physiological vWF-cleaving enzyme activity.

According to the invention, these objects are achieved by a protein comprising an enzyme activity purified according to the present specification, which is named "multimerase" because of its proteolytic activity relative to von Willebrand factor multimers and has the following properties:

a) it has an indirect or a direct proteolytic activity and converts vWF having a singlet structure to vWF having a satellite structure, b) it is active in the presence of the serene protease inhibitor diisopropyl fluorophosphate (DFP) or of the calpain protease inhibitor Z-Leu-Leu-Tyr-$CHN_2$.

Property a) can be determined by a simple test in which a recombinant vWF having singlet structure is treated with the multimerase, which test is explained in more detail in the Examples, and this property is a completely new property of proteases and so far is unique to the multimerase according to the invention. The satellite structure, e.g. triplet structure, corresponds to a multimer pattern after electrophoretic analysis of plasmatic vWF which is characterized by central bands and several satellite bands (cf. FIGS. 12 and 13).

The terms "direct" and "indirect" indicate that the multimerase according to the invention has direct proteolytic activity mediated without an activator, or that it contributes to enhanced proteolytic activity via an appropriate activating effect or a mediator.

Preferably, the multimerase has an optimum proteolytic activity at a pH ranging from 7 to 10, preferably at a pH of from 7.5 to 8.5. However, this optimum pH range is largely dependent on the (ionic) environment in which the reaction is carried out.

Preferably, the multimarase is provided in a fraction obtained upon gel filtration of a plasma or serum fraction corresponding to the molecular weight of more than 200 kD, preferably around 300 kD.

Preferably, after a purification according to the invention, the multimerase is provided in at least 1,000-fold, preferably at least 10,000-fold enriched form as compared to plasma.

Preferably, the purified multimerase has a specific activity of at least 10 U/mg protein in the presence of a serine protease inhibitor. One unit is defined as that enzyme activity which is contained in one milliliter of human normal plasma or can be generated therefrom, respectively.

It has been shown that the multimerese is particularly active in the presence of or after incubation with, respectively, bivalent metal ions, such as alkaline earth ions, in particular $Ba^{2+}$, $Sr^{2+}$, $Ca^{2+}$ and $Mg^{2+}$, and that its activity can be further increased by shear stress, reduced ionic strength or chaotropic agents.

The activity of the multimerase is especially generated if the ionic strength of the environment is lowered to below the physiologic ionic strength, in particular corresponding to a concentration of less than 15 mM Tris. The shearing forces which may act when flowing through a capillary, when stirring in containers or when passing through a nozzle or generally on account of a mechanical action on the multimerase or its substrate, respectively, substantially contribute to the increased activity of the multimerase. It is presumed that the effect of chaotropic substances is due to the partial or complete change of the tertiary structure of a protein. These substances include salts, such as ammonium sulphate, calcium chloride, thiocyanates, but also urea and guanidinium chloride.

Preferably, the multimerase preparation according to the invention has an increased activity relative to modified vWF, such as partially denatured vWF or vWF having a conformation change.

The multimerase according to the invention can be inhibited by not effecting or stopping activation. Thus, chelating agents, such as EDTA, EGTA and citrate, which have an inhibiting effect on the metalloenzyme, can be used as inhibitors. The activity of the multimerase may, however, also be inhibited by vWF peptides corresponding to the Tyr842-Met843 peptide sequence which can block the binding site of the multimerase. Lowering of the temperature, e.g. by freezing the multimerase-containing fraction, also results in a reduction of the multimerase activity.

In a further aspect, the present invention relates to a method of purifying the multimerase according to the invention from plasma, serum, or from a fraction of plasma or serum, by a chromatographic procedure, the purified multimerase being recovered from those fractions in which the proteolytic activity is found for the inactivation of vWF in the presence of a serine protease inhibitor, preferably aprotinin.

The invention also relates to a preparation comprising a 1,000-fold, preferably 10,000-fold enriched multimerase as compared to plasma.

The present invention also relates to a method of producing a vWF having a satellite structure, by incubating a vWF having a singlet structure with a multimerase according to the invention, whereby a vWF having a satellite structure is obtained and the vWF is recovered.

The method is preferably carried out under nearly physiological conditions. For instance, the conversion of the vWF is effected at a pH ranging from 7 to 10, preferably 7,5 to 8.5, and at a temperature of from 20 to 40° C., preferably approximately room temperature, for a period of time which suffices for the formation of satellite bands without substantially affecting the activity of the vWF.

For this preparation of the vWF having satellite structure, preferably a multimerase is used which, as described before, develops an optimum activity under certain conditions, e.g. by pre-incubation with metal ions. The duration of the reaction also depends on the enzyme/substrate ratio, which is selected in a range of from 0.01:1 to 100:1, preferably within a range of from 0.1:1 to 10:1, most preferred is the physiological ratio of approximately 1:1 (unit per unit). The reaction is either stopped by the addition of a suitable inhibitor, in particular of a chelating agent, or by lowering the temperature, e.g. by freezing the reaction solution, or by stopping the reaction by not generating the activity. The course of the reaction can be monitored by electrophoretic analysis, and a suitable end can be determined.

This preparation of the vWF having satellite structure can be effected both in vitro in a suitable reaction environment, and in viva or ex vivo, e.g. by the expression of r-vWF in a cell culture or extracorporeally.

Incubation of the multimerase with the biologically active vWF is preferably carried out in the presence of a serine protease inhibitor, since by the incubation in the presence of a serine protease inhibitor, unspecific proteolytical processes are avoided which are not directly related to the multimerase and which are caused by serine proteases present in blood or in plasma. The proteolytic activity of a possibly contaminating serine protease can be avoided under the protection of such an inhibitor.

Preferably, the multimerase according to the invention is thus obtained in a fraction which is substantially free from a serine protease activity, corresponding to a plasmin activity of less than the detection limit of a test by using a specific chromogenic substrate, e.g. S2251 according to EP-0 353 218.

In another aspect, the present invention relates to a pharmaceutical composition comprising a purified "multimerase" activity according to the present invention which has the following properties:

a) it has an indirect or a direct proteolytic activity and converts vWF having a singlet structure to vWF having a satellite structure, b) it is active in the presence of the serine protease inhibitor diisopropyl fluorophosphate (DFP) or of the calpain protease inhibitor Z-Leu-Leu-Tyr-$CHN_2$, and c) it is treated for inactivation or removal of viruses.

For Properties a) and b): See Above

The virus inactivation or removal treatment may be performed by any treatment accepted as being efficient. According to preferred embodiments of the present invention, the pharmaceutical composition comprising the multimerase activity is treated with tensides and/or heat, e.g. by a heat treatment in the solid state, especially a steam treatment according to EP-0 159 311, or EP-0 519 901, or EP-0 674 531.

Further treatments for inactivation of viruses also comprise treatment by chemical or chemical/physical methods, e.g. with chaotropic agents according to WO94/13329, DE 44 34 538 or EP-O 131 740 (solvents), or photoinactivation.

Nanofiltration also represents a preferred method of depleting viruses within the scope of the present invention.

According to a further aspect, the present invention relates to the multimerase according to the invention as a drug, in particular the use of the multimerase according to the invention for the prevention and therapy of thromboses or thromboembolic disorders, preferably for the prevention and therapy of a supranormal vWF level or of an increased level of high-molecular vWF by administering to a patient an effective dose of a multimerase-containing pharmaceutical preparation.

This supranormal vWF level may be caused by a supranormal vWF antigen concentration or a supranormal vWF activity, activity in particular referring to the primary hemostatic activity, but also to the binding activity to the subendothelium, to the thrombocytes, to the thrombocyte-adhesion proteins, such as GPIb and GPIIb/IIIa complex, to collagen, to factor VIII and to heparin.

Preferably, the present invention relates to the prevention and therapy of thrombotic thrombocytopenic purpura, Henoch-Schönlein purpura, hemolytic-uremic syndrome and preeclampsia or neonatal thrombocytopenia.

Thrombotic thrombocytopenic purpura (TTP) was first described by Moachcowitz, 1924, and is characterized by thrombocytopenia with normal megakaryocyte number in bone marrow, microvascular thromboses, hyaline thrombi, restricted function of the kidneys and endothelial cell proliferation. The pathological and clinical results in patients suffering from TTP suggest a direct thrombooyte-aggregating stimulus in the microcirculation.

In addition to thrombocytopenia, the clinical picture includes intravascular hemolysis with fragmented erythrocytes and neurological symptoms. Incidence in the normal population is estimated at 0.1/100,000/year. In HIV infected individuals, it is approximately 4/100,000. Different types of TTP seem to exist. Beside a primary TTP, also so-called secondary TTPs are found in connection with pregnancy, chemotherapy, bone marrow transplantation and autoimmune diseases. With chronic relapsing TTP (CRTTP), there are frequent episodes at regular intervals. Unusually high multimeric forms of vWF which are liberated by endothelial cells are found in plasma from patients afflicted with TTP. Under "shear stress", these unusually large vWF multimers bind to glycoprotein Ib and glycoprotein IIb/IIa much more strongly than normal vWF and cause the intravascular thrombocyte aggregation.

Attacks of TTP are difficult to treat. In most instances, the aim is to remove the high-molecular vWF multimers by plasma exchange.

Henoch-Schönlein purpura (HSP) is a clinical syndrome characterized by non-thrombocytopenic purpura, arthralgias and glomerulonephritis. Patients afflicted with HSP have an abnormal vWF multimer picture with supranormal high molecular weight vW multimers. Detection of these supranormal vW multimers in HSP suggests an impaired endothelial cell function. Multimers of low molecular weight are delivered by the endothelial cells in a so-called constitutive mechanism, while the high molecular weight multimers are liberated from the "Weibel/Palade bodies" of the endothelial calls upon stimulation.

The pharmaceutical preparation according to the Invention is produced by purifying a multimerase-containing starting material, preferably by chromatographic methods, such as ion exchange chromatrography, hydrophobic chromatography or affinity chromatography, and subsequently finishing it by known methods, optionally by reshining it with suitable buffer, auxiliary, preserving and/or stabilizing substances or protease inhibitors, respectively, and filling it into containers into a form suitable for administration, and preferably packing it so as to be storage-stable, optionally in the lyophilized or frozen state.

The effective dosage of the preparation when applied will vary, depending on the respective syndrome, and preferably should be chosen after determination of the endogenous vWF protease activity in the patient [e.g. by means of the determination method according to the invention (infra)]. The dosage also depends on whether or not the parenteral, preferably intravenous, subcutaneous or intramuscular administration is to be effected in bolus form, and whether it is to be effected systemically and/or locally at the site of thrombosis.

When administering the preparation according to the invention, the vWF plasma concentration as well as the structure of the vWF and the vWF protease activity in the patient should be monitored, and dosage should be optimized on the basis of these data.

The preparation according to the invention may be produced both by purification from blood, serum or plasma, and by a respective expression system.

A preparation according to the invention may also be provided by expression of the multimerase in vivo or ex vivo. Suitable for this are above all calls derived from mammals, in particular human cells, which can be cultured and optionally introduced into the patient. Within the scope of a gene therapy, it is possible to insert the nucleic acid encoding the multimerase into the cells, in particular into arterial endothelial calls, which are capable of expressing the multimerase in vessels or in vessel prostheses, respectively.

For this technology, a nucleic acid encoding the multimerase can be provided in a known manner. A pre-requisite is a purified multimerase which can be used as a template for the nucleic acid. This nucleic acid may be inserted either via a vector or directly into the host cell, where expression of the multimerase is affected in a known manner.

Preferred chromatographic purification methods are ion exchange chromatography, affinity chromatography or gel filtration, combinations of these methods and multiple chromatographies being considered particularly preferred.

Yet another aspect of the present invention relates to a method of assaying the proteolytic activity of the multimerase according to the present invention. To detect the multimerase activity, a method is used which comprises the following steps: incubating a fraction containing the multimerase with a vWF, and determining the reaction rate of vWF. The fraction is, for instance, a plasma sample or a plasma fraction or a fraction with the enriched, possibly purified, multimerase. The latter is contacted with a vWF which may be a native human vWF, preferably having a singlet structure, or with a corresponding vWF fragment containing the Tyr842-Met843 peptide sequence.

Incubation is preferably effected under conditions which ensure an optimum activity of the multimerase, as described before. During the incubation which is preferably carried out under nearly physiologic conditions, at pH 7 to 10, preferably pH 7.5 to 8.5, at 20 to 40° C., preferably approximately room temperature, vWF is reacted, degraded or inactivated, respectively, aid the result of the reaction can be determined. What is detected are, e.g., vWF degradation products and fragments, such as multimers of low molecular mass or satellite bands after electrophoretic analysis, or the change of the activity of vWF.

In the method according to the invention, incubation of the multimerase with the biologically active vWF is preferably carried out in the presence of a serine protease inhibitor, and the reaction rate preferably is determined by the extent of inactivation or by the formation of certain fragments or satellite bands of the vWF.

By incubation in the presence of a serine protease inhibitor, such as aprotinin, unspecific proteolytic processes which cannot be directly traced back to the multinerase and which are caused by serine proteases present in blood or plasma can be avoided.

Determination of the proteolytic activity of the multimer according to the invention may, however, not only be carried out by direct conversion of the vWF, but also by cleavage of a chromogenic substrate comprising a peptide sequence homologous with the vWF peptide binding sequence Tyr842-Met843 as well as a chromogenic group, by cleaving the substrate under the action of the multimerase and forming a chromophore, whereupon colour development is determined which can be viewed as directly proportional to the proteolytic activity of the multimerase.

Furthermore, the invention also relates to vWF preparations that have been produced free from multimerase activity and in particular in the absence of a multimerase activity. These vWF preparations preferably contain the native vWF which contains the entire spectrum of the multimers and which is characterized by a low degree of cleavage of the Tyr842-Met843 peptide bond. Alternatively, however, a vWF fraction, vWF, a vWF derivative or a vWF fragment or a vWF mutant can be contained, with the proviso that it contain the Tyr842-Met843 peptide sequence. This preparation above all is suitable for the production of pharmaceutical preparations, since, due to the lack of multimerase activity, they remain unchanged even after prolonged storage, e.g. in the liquid state.

The vWF preparations according to the invention can be provided by specific Inhibition of the multimerase or by separation or depletion of the multimerase by means of the afore-mentioned chromatographic purification methods, in particular by immunoaffinity chromatography by using antibodies directed against the multimerase. Inhibition can be obtained by a content of a chelating agent in the pharmaceutical preparation or by specific inhibitors which bind like a "substrate mimic" to the active center of the multimerase, thus inhibiting the activity in competitive manner.

The pharmaceutical vWF preparation containing a reduced multimerase activity, in particular of less than the detection limit, preferably further comprises the blood coagulation factor VIII, a factor VIII derivative or a factor VIII mutant, stabilized by complex formation to the vWF. Since the multimer pattern in the vWF preparation according to the invention surprisingly remains unchanged even over an extended period of time, i.e. is permanent, also the stabilizing effect for factor VIII in the pharmaceutical preparation according to the invention remains unchanged and permanent even after an extended storage in the liquid state.

The pharmaceutical preparation according to the invention thus is storage-stable not only in the lyophilized or liquid-deep-frozen states, but also as a liquid preparation.

By aid of the multimerase according to the invention, it is furthermore possible to define resistant forms of the vWF. Certain vWF fractions, derivatives or mutants are accordingly incubated with a fraction containing a defined multimerase-activity, and the extent of proteolytic degradation is determined. A resistent form of vWF is present if the multimerase activity does not substantially influence the vWF activity (e.g. by altering the Tyr842-Met843 peptide sequence). This resistant form of vWF can be utilized to stabilize FVIII:C in vitro and in vivo. Thereby not only the half-life of the vWF form in vivo is extended, but also the residence time of FVIII:C in plasma.

Finally, the present invention also relates to a method of producing antibodies against the multimerase according to the invention, which is carried out in that a preparation containing the enriched, optionally purified multimerase according to the invention is used as an immunogen, and respective polyclonal or monoclonal antibodies against the multimernase are produced in a manner known per se.

Furthermore, the present invention also relates to an antibody preparation containing antibodies against the multimerase, wherein the antibody preparation may be monoclonal or polyclonal.

Preferably, the antibodies according to the invention are immobilized on a solid phase and may thus be used for immunological detection or for the purification of the multimerase.

FIG. 4 shows the degradation of vWF by various blood components;

FIGS. 7 (panels A and B) shows an SDS-PAGE of the fractions obtained after Sephacryl S-300 HR chromatography;

FIG. 9 (panels A and B) shows the effect of protease inhibitors on the vWF degradation:

FIG. 11 shows the effect of vWF protease on fibrinogen, BSA, collagen from calf skin and diluted normal plasma (protease panel and control panel have lanes A–D);

FIG. 12 (panels A and B and C) shows the degradation of vWF by the multimerase according to the invention;

FIG. 13 (panels A and B and C) shows the degradation of vWF from cryoprecipitate with the multimerase according to the invention;

FIG. 14 (panels A and B, C and D) shows the degradation of vWF high multimers and I-vWF by means of the multimerase according to the invention;

FIG. 15 (panels A and B and C) shows the degradation of r-vWF with plasmin;

FIG. 16 (panels A and B and C) shows the degradation of r-vWF with plasmin with and without inhibitors;

FIG. 17 (panels A and B) shows the degradation of vWF from cryoprecipitate with plasmin.

The present invention is further explained by the following examples, which do not limit the invention in any manner.

EXAMPLES

Purification of vWF vWF was purified by gal filtration of human cryoprecipitate, obtained from 1 l citrated plasma, an a 2.6×35-cm column of Sepharose CL-2B (Pharmacia, Uppsala, Sweden). Elution was performed with 0.13 M sodium chloride, 0.01 M citrate, 0.01 M Tris-HCl, pH 7.4. Fractions of 6 ml were collected at a flow rate of 24 ml/h. vWF antigen was measured by ELISA by using polyclonal rabbit antiserum against human vWF (RAHu/FVIII, from Nordic (Tillburg, The Netherlands), peroxidase-labeled rabbit antihuman-vWF, mouse monoclonal antibody against rabbit IgG (M737), and the kit for immunostaining (K670) (all from Dako (Glostrup, Denmark)), according to the instructions included with the kit.

Figure 1A:
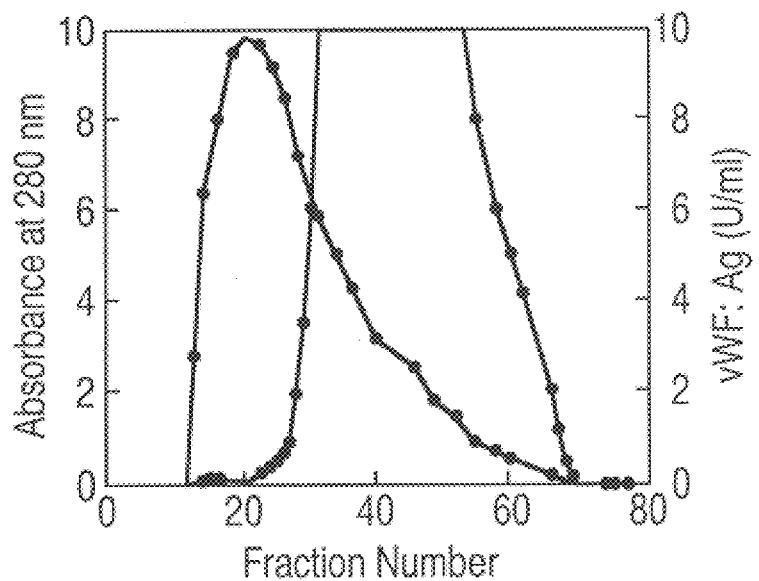
FIG. 1 (panels A and B) shows the purification of vWF.
Figure 1B:
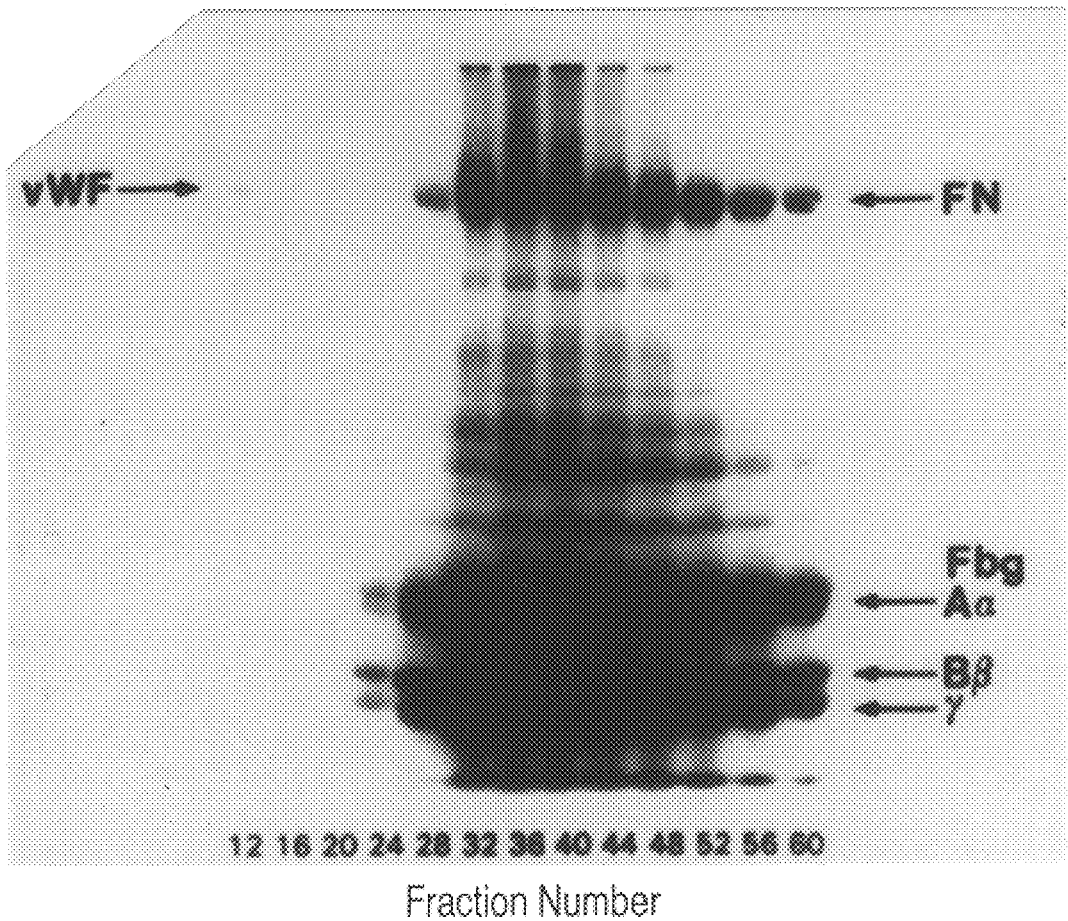

The results of vWF-purification are illustrated in FIG. 1 (panel A (graph) and panel B (gel)): Fractions 12 to 20 contained vWF substantially free from contaminating proteins. These fractions were used as the substrate in determining the vWF cleavage activity (infra).

Figure 2A:
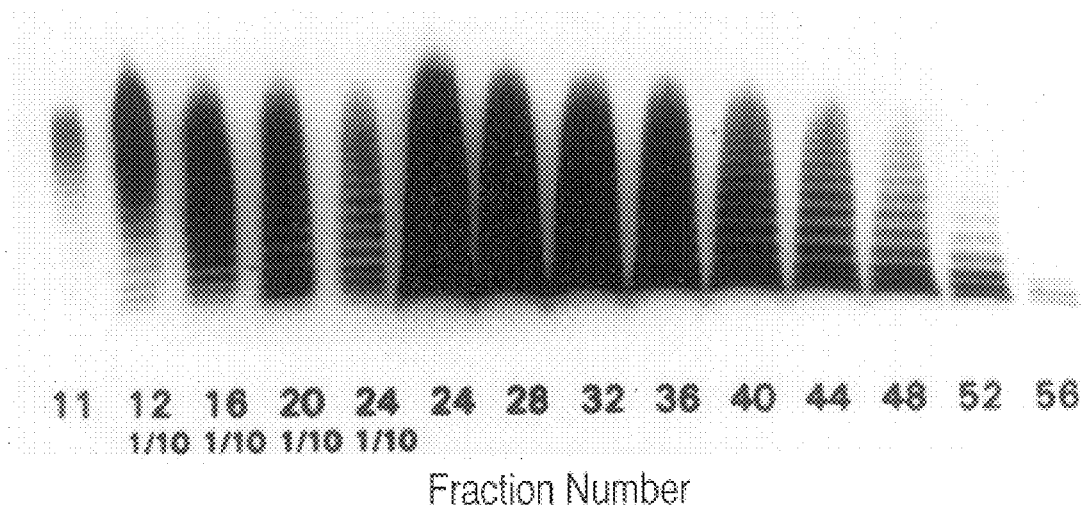
FIG. 2 (panels A and B) shows the degradation of vWF by contaminating proteases.
Figure 2B:
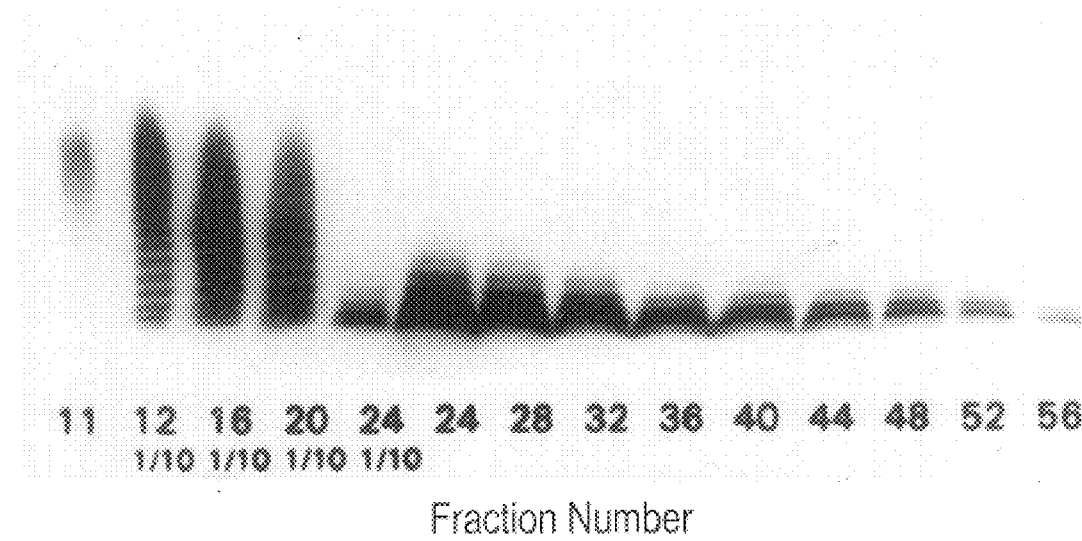

The vWF contained in these fractions proved to be very stable; even after a 24 h dialysis incubation at 37° C. (in the absence of inhibitors), a multimer pattern identical to that of the untreated fractions was obtained, both, with the 24 h dialysis against 0.13 M sodium chloride, 0.01 M citrate, 0.01 M Tris-HCl, pH 7.4, and with the 24 h dialysis against 1 M urea, 5 mM Tris-HCl, pH 7.4. SDS agarose gels of these assays are illustrated in FIG. 2 (panels A and B).

The subsequent fractions, however, showed a pronounced vWF degradation at low salt concentrations in the presence of urea.

Figure 3:
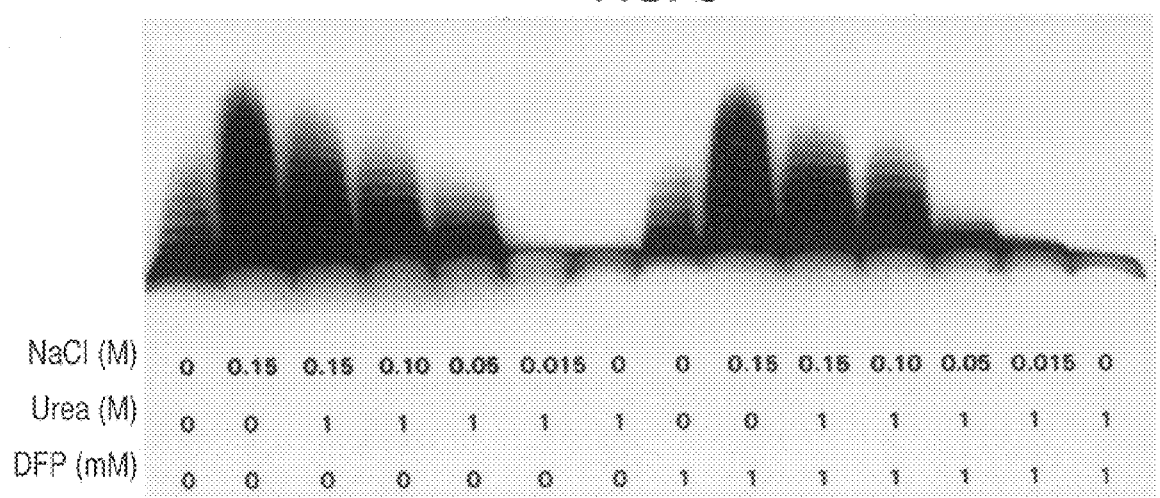
FIG. 3 shows the effect of salt and urea on the cleavage of vWF.

Effect of the salt and urea concentrations on the cleavage of vWF;

Aliquots of the fraction No. 29 from the sepharose CL-2B column were dialyzed against a 5 mM Tris-HCl (pH 7.4) solution of varying salt concentrations, in the presence or absence of urea, no calcium ions being added. Parallel assays were performed with further aliquots of fraction 29 which had been subjected to a 5 minute incubation with 1 mM DFP prior to dialysis. From FIG. 3 it is apparent that the large vWF multimers disappeared after dialysis, if no sodium chloride was present. Moreover, the vWF degradation could be increased markedly by 1 M urea even at physiological salt concentrations. The combination of a low salt concentration with 1 M urea led to the complete degradation of vWF. A preincubation with 1 mM DFP, a strong serine protease inhibitor, yielded identical results. Thus, dialysis at 37° C. against 1 M urea, 5 mM Tris-HCl was chosen as an optimum condition for a sensitive assay for determining the protease activity.

Assay of the vWF Cleaving Activity

Because, as has been mentioned, the degradation of vWF was found to be strongly dependent on the buffer conditions used, the enzyme and the substrate were incubated on a circulary dialysis membrane (Millipore VSWP; diameter, 25 mm; from Millipore (Bedford, USA)), the surface being incubated with 50 ml of dialysis buffer. The buffer system which had been sufficiently optimized for the instant assaying system thus comprised a dialysis Solution with 1 M urea in 5 mM Tris-HCl at pH 8. Full activation of the protease was achieved by preincubation for 5 minutes at 37° C. with 10 mM barium chloride. In a typical experiment, 50 µl activated protease solution and 100 µl substrate solution were carefully placed on a floating membrane, and incubated in a closed tube for 24 h in a dry oven at 37° C.

Protease-free fractions of vWF from the Sepharose CL-2B column were used as substrate solution, the vWF concentration in the incubation mixture was about 30 µg/ml. The reaction mixtures were then removed from the surface of the membrane filters and subjected to SDS-agarose gel electrophoresis to examine the multimeric pattern of vWF.

SDS-agarose Gel Electrophoresis and Immunoblotting of Unreduced vWF

Thin-layer agarose electrophoresis was performed using the discontinuous buffer system as described by Ruggeri and Zimmerman (Blood 57 (1981), 1140). Before electrophoresis, each sample was incubated with an equal volume of the SDS-containing sample buffer for 15 minutes at 60° C. The horizontal electrophoresis was performed in 1% HGT(P) agarose (2 mm thick, 20 cm wide, and 8.5 cm long) for 17 h at 16° C. in an LKB multiphor apparatus (Pharmacia-LKB) at 80V and 10 mA. The proteins were electrotransferred to a nitrocellulose membrane (from Schleicher & schuell (Dassel, Germany) for 3 hours at 26 V and 1.4 A using a Trans-Blot cell from Bio-Rad with a buffer containing 0.04% SDS and 0.05 M phosphate, pH 7.4. vWF multimers were identified with peroxidase-conjugated antibodies against human vWF (with perozidase-labelled rabbit-antihuman-vWF antibody P226 from Dako (Glostrup, Denmark)).

SDS-PAGE

SDS-5% polyacrylamide gels were prepared according to Laemmli (Nature 227 (1970), 680). The proteins were reduced with 65 mmol DTT for 15 minutes at 60° C. Unreduced and reduced chromtatographic fractions from the Sephacryl S-300 HR column were electrophoretically separated in 3-mm-thick gels for 18 hours at 60 V and were stained with Coomassie Blue.

Immunoblotting of Reduced vWF

Reduced samples of undegraded and proteolytically cleaved vWF were subjected to SDS-PAGE and were electrotransferred to nitrocellulose as described above. For detection of vWF fragments, the nitrocellulose was incubated with a rabbit antiserum against human vWF (RAHu/FVII), followed by incubation with mouse antibodies against rabbit IgG (M737; from Dako (Glostrup, Denmark)) and the APAAP (alkaline phosphatase anti-alkaline phosphatase) reagent (K670 from Dako (Glostrup, Denmark)) according to Furlan et al. (PNAS 90 (1993), 7503).

Preparation of Blood Components to be Tested for the Presence of the Protease Whole blood was drawn from normal individuals into a glass tube without the addition of anticoagulants. After 15 minutes at room temperature, the clotted blood sample was centrifuged twice for 15 minutes at 2,500 g. Subsequently, 10 µl of 10 mM PPACK (Diphenylalanylprolyl arginine-chloromethylketone from Bachen, Bubenderf, (Switzerland)) was added to 10 ml serum, and the sample was incubated for 10 minutes at room temperature and frozen at −20° C. From the same subject, 90 ml of blood was drawn into 10 ml of 0.13 M sodium citrate in a plastic bottle. After centrifugation for 15 minutes at 300 g, about 50 ml platelet-rich plasma (PRP) was recovered. One aliquot of PRP was centrifuged for 15 minutes at 2,500 g. The resulting platelet-poor plasma (PPP) was recentrifuged for 15 minutes at 3,000 g and frozen at −20° C. The platelet sediment was resuspended in 0.9% sodium chloride in 1/15 of the original volume and subjected to 3 cycles of freezing and thawing. The lysed platelets were centrifuged for 15 min at 3,000 g, and the resulting supernatant and the sediment were frozen at −20° C. A frozen aliquot of the PPP was slowly thawed to produce the cryoprecipitate. After centrifugation for 15 minutes at −5° C. and 3,000 g, supernatant as well as cryoprecipitate, taken up in 1/15 of the original volume of 0.9% sodium chloride, were frozen at −20° C. Another aliquot of PPP was transferred to a glass tube, mixed with 1/40 volume of a 1 M calcium chloride solution and incubated for 15 minutes at 37° C. After removal of the fibrin clot and 15-minute centrifugation at 3,000 g, PPACK was added to a final concentration of 25 μM, and the defibrinated plasma was frozen at −20° C. The frozen samples were incubated for 10 minutes each at 37° C. before the assay for determining the protease activity.

Assaying Prepared Blood Components for Protease Activity

10 μl of 10 mM PPACK and 10 μl of 0.55 M calcium chloride was each admixed to 200 μl serum, PPP, cryoprocipitate-free PPP, defibrinated PPP as well as 15-fold concentrated cryoprecipitate and lysed platelets. After incubating for 10 minutes at 37° C., 10 μl aliquots were mixed with 40 μl vWF solution, dialyzed against 1 M urea, 5 mM Tris-HCl (pH 7.4) over night at 37° C., and the proteolytic degradation of vWF detected by SDS agarose gel electrophoresis.

It was found that protease activity was considerably higher in PPP than in the supernatant or the sediment of lysed platelets obtained from a 15-fold concentration of PRP (of. FIG. 4). The protease activity was not affected by defibrination and was partially recovered in the cryoprecipitate of PPP; the otyopreoipitate corresponding to a 15-fold concentrated PPP showed considerable activity, but the nonconcentrated cryoprecipitate contained much less protease than did the equivalent amount of PPP. There was no significant difference in the protease activity found in citrated PPP and in serum obtained from non-coagulated blood.

Purification of Protease from Plasma

Fibrinogen was removed from plasma before chromatographic procedures were performed, because these purification procedures might induce activation of the coagulation cascade. Experiments also indicated that the activity of the vWF-degrading protease was not—or not substantially— affected by defibrination of plasma or of the plasma fraction, DFP or PPACK.

Blood (450 ml) from healthy individuals was collected Into 63 ml citrate/phosphate/dextrose/adenine (CPD-A) solutions on a shaking balance. After 2 centrifugations for 15 minutes at 20° C. and 2,500 g, 1 M calcium chloride was added to a final concentration of 25 mM, and the recalcified PPP was stirred for 30 minutes at 37° C. After removal of the fibrin clot by centrifugation, PPACK and DFP were added to the resulting serum to final concentrations of 5 μM and 2 μM, respectively, and incubated for 15 minutes at 37° C. to inhibit the activated clotting enzymes. Moreover, the serum was dialyzed against the equilibrating buffer with 1 M sodium chloride and 0.05 M Tis-HCl at pH 7.4. 50 ml aliquots were stored at −20° C. until purification.

Figure 5A:
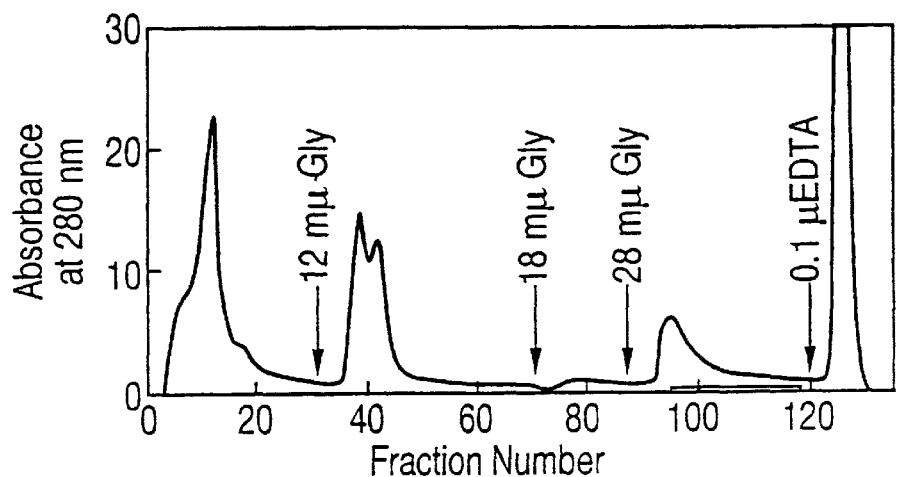
FIG. 5 (panels A and B and C) shows the purification of the proteins from plasma.
Figure 5B:
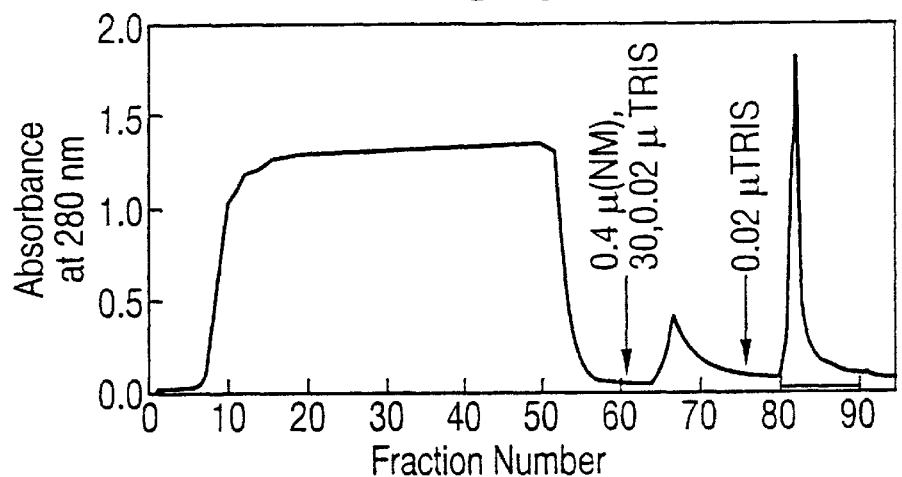
Figure 5C:
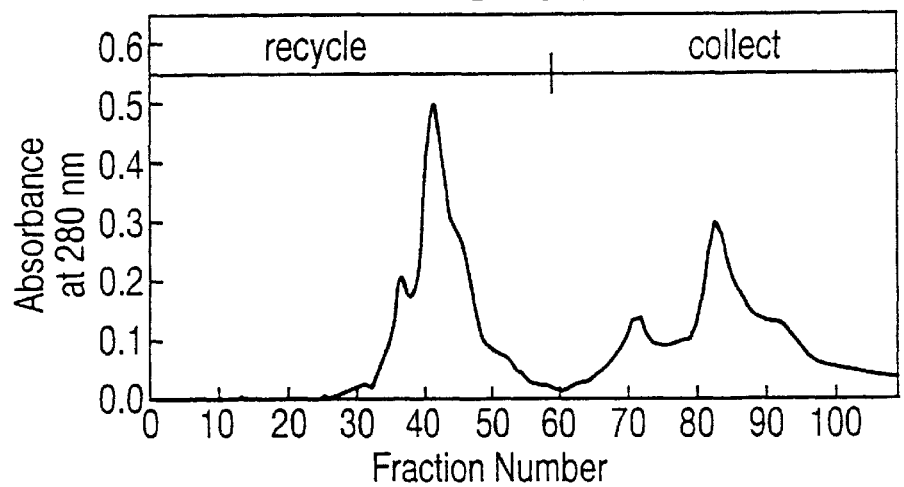

The protease could first be purified from the defibrinated normal plasma as starting material on $Cu^{2+}$-loaded chelating Sepharose (1.6×22 cm; Pharmacia LKB) using step-wise elution with equilibrating buffer containing increasing glycine concentrations. Protease-containing fractions (cf. horizontal line in FIG. 5 (panel A) were pooled (this pool containing 14.7% of the original protein), dialyzed against 0.6 M $(NH_4)_2SO_4$/0.02 M Tris-HCl, pH 7.4, and applied onto a column filled with butyl sepharose (1.6×27 cm: Pharmacia LKB), most of the contaminating proteins being removed by step-wise elution at a lower $(NH_4)_2SO_4$ concentration. Proteolytically active fractions (cf. transverse line in FIG. 5 (panel B) from two butyl sepharose columns were pooled (this pool containing nearly all the protease activity, yet only 0.75% of the original protein), dialyzed against 1 mM EDTA, lyophilized, taken up in 5 ml distilled water and applied on a Sephacryl S-300 HR column (2.6×90 cm; Pharmacia, LKB) that had been equilibrated with 0.15 M NaCl, 0.01 M Tris-HCl, pH 7.4 (cf. FIG. 5 (panel C); the fractions below the cross-section contained the entire protease activity, yet only 0.08% of the original total protein).

To improve the resolution of gel filtration, a long column was simulated by closing the first elution cycle, by reintroducing the eluted proteins into the same column and collecting them in a second cycle. Again, the active fractions were pooled, dialyzed against 1 mM EDTA, lyophilized, redissolved in 3 ml distilled water and submitted to a further gel filtration on a Sephacryl S-300 NR column.

In this gel filtration, the first two cycles were closed and the fractions were collected in the third cycle. In all these depicted chromatographic procedures, fractions of 6 ml were collected at a flow rate of 60 ml/h. Fractions containing the protease were stored at −20° C.

Figure 6A:
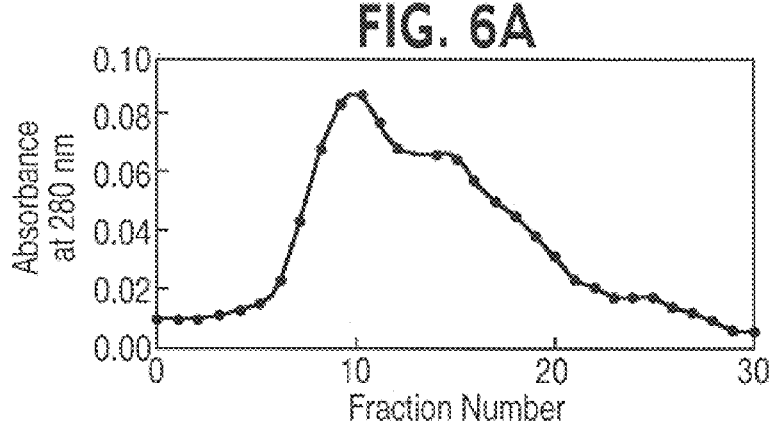
FIG. 6 (panels A and B) shows the chromatography of the protease on Sephacryl S-300 HR.
Figure 6B:
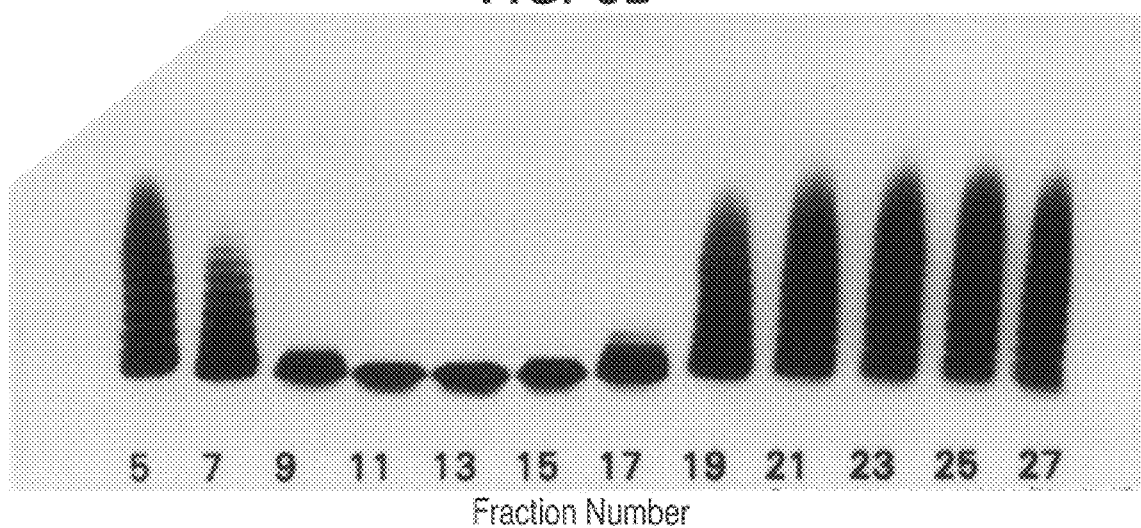

The results are illustrated in FIG. 6 and show the elution of the UV-absorving material (FIG. 6 (panel A)) and of the protease activity (FIG. 6 (Panel B)). The peek of the protease activity (fractions 9 to 17) contained merely 0.009% of the original serum protein. Thus, a purification factor of approximately 10,000 was reached. Nevertheless, the protease preparation obtained still contained substantial amounts of contaminating proteins (cf. FIG. 7). The peak of the protease activity (fractions 11 to 15) occurred together with a protein band in the unreduced gel with a molecular weight of approximately 300 kD, which appeared with several proteins with a molecular weight ranging between 130 and 450 kD (main bands with $M_r$ of 450, 200, 180 and 130 kD).

Amino Acid Composition and Sequence Analysis

For analysis of the amino acid composition and of amino acid sequence, the unreduced peak fraction of the protease and the reduced vWF fragments were dialyzed against 1 mM EDTA, were lyophilized, and were redissolved in 1/50 of the original volume before SDS-PAGE. The HMW protein bands were electrotransferred from the gel to a PVDF (polyvinyliden-difluoride) membrane (BioRad) for 6 hours at 26 V and 0.4 A, using 0.05% SDS, 10% methanol, 0.05 M boric acid, pH 9.0, as transfer buffer. After transfer, the membrane was stained with Coomassie-Blue in 40% methanol, destained in 40% methanol and 10% acetic acid, and air-dried. The excised bands were transferred to the blot cartridge of the Applied Biosystems Model 477A sequenator, which was equipped with on-line high-performance liquid chromatography for analysis of phenylthiohydantoin derivatives, For analysis of amino acid compositions, the protein bands were hydrolyzed in the gas phase over 6N HCl for 22 hours at 110° C. The amino acids were extracted from the PVDF membrane with 70% 0.1 N HCl/30% methanol and were determined by high-performance liquid chromatography as phenylthiocarbamyl derivatives. The amino acid composition of the unreduced protein band coeluted from the Sephacryl S-300 HR column together with the protease activity is shown in Table 1.

TABLE 1

| Amino Add | Residues per 1,000 Residues |
| --- | --- |
| Asp + Asn | 99.4 |
| Thr | 59.4 |
| Ser | 63.3 |
| Glu + Gln | 150.2 |
| Pro | 65.5 |

TABLE 1-continued

| Amino Add | Residues per 1,000 Residues |
|---|---|
| Gly | 75.9 |
| Ala | 86.5 |
| Val | 70.7 |
| Ile | 32.9 |
| Leu | 101.7 |
| Tyr | 30.6 |
| Phe | 41.7 |
| His | 22.4 |
| Lys | 41.6 |
| Arg | 49.3 |

Influence of Metal Ions and pH on the Activity of the vWF-cleaving Protease

Aliquots (95 μl) of the purified protease were preincubated for 15 minutes at 37° C. with 5 μl of 0.2 M solutions of the following salts: $ZnCl_2$, $CuSO_4$, $Cd(CH_3COO)_2$, $CoSO_4$, $NiCl_2$, $MnCl_2$, $MgCl_2$, $CaCl_2$, $SrCl_2$ and $BaCl_2$. Then, 50 μl of the purified vWF was added to each aliquot, and the incubation mixtures were transferred onto floating membrane filters. After incubation for 24 hours at 37° C. against 1 M urea, 5 mM Tris-HCl, pH 7.4, the samples were removed from the filters and applied to SDS-agarose gel electrophoresis.

The protease showed no activation by $Zn^{2+}$, $Cu^{2+}$, $Cd^{2+}$, $Co^{2+}$, $Ni^{2+}$ or $Mn^{2+}$. Only slight activation by $Mg^{2+}$ was found; substantial activation could be obtained by $Ca^{2+}$, $Sr^{2+}$, and in particular by $Ba^{2+}$ (cf. FIG. 8 (panel A).

Prolonged preincubation with calcium, strontium and barium was associated with a loss of protease activity even at physiological salt concentrations and in the absence of urea, probably because of autodigestion of the protease. In the absence of these ions the protease was quite stable in solution, and thus it was possible to purify the enzyme by chromatographic procedures taking place for several days at room temperature.

pH-optima of the protease after activation by calcium and barium were determined by preincubating the protease with 10 mM calcium chloride or with 10 mM barium chloride and incubating with vWF during the dialysis in urea Tris-HCl buffer, several buffers having a pH ranging between 6 and 11 being used. The multimer pattern of vWF in the dialyzed samples were analyzed with SDS agarose electrophoreais.

Figure 8A:
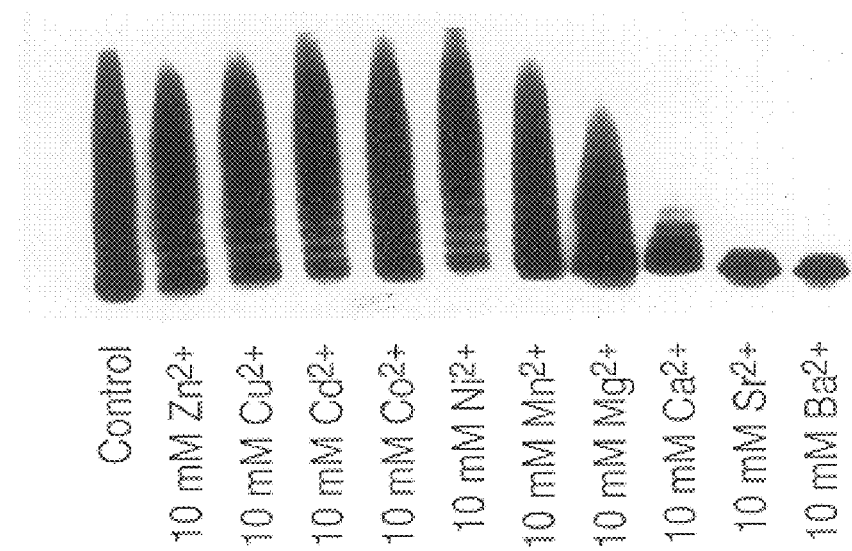
FIG. 8 (panels A and B) shows the influence of metal ions and pH on the activity of the vWF-cleaving protease.
Figure 8B:
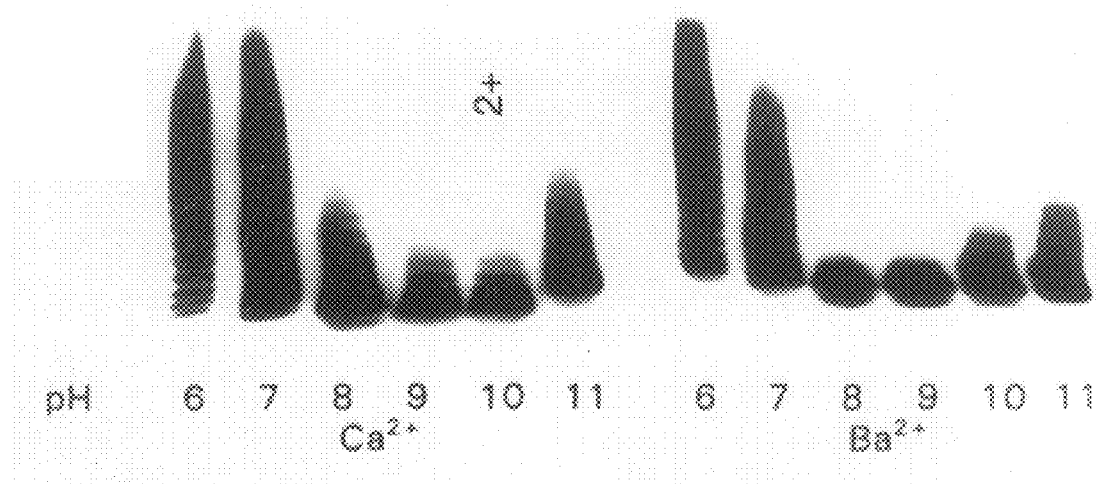

The pH optimum for vWP degradation by the calcium-activated protease was found at 9 to 10, whereas the highest activity of the barium-activated protease was at approximately pH 8 (cf. FIG. 8 (panel B)).

The experiments for determining the vWF-degrading protease activity thus were always performed at pH 8 after an incubation with 10 mM barium chloride.

Effect of Protease Inhibitors on vWF Degradation

Purified protease was reactivated with 10 mM barium chloride for 5 minutes at 37° C. and subsequently incubated for 15 minutes at 37° C. with the following protease inhibitors: EDTA (final concentration 10 mM), EGTA (10 mM), $Na_3$-citrate (10 mM) iodoncetamide (IAA, 10 mM), N-ethylmaleimide (NEM; 10 mM), DFP (1 mM), phenylmethylsulfonyl fluoride (PMSF; 1 mM), N-α-p-tosyl-L-lysine-chloromethylketone (TLCK; 1 mM), N-α-p-tosyl-L-phenylalanine-chloromethylketone (TPCK; 1 mM), leupeptin (0.01 mM) and aprotinin (0.01 mM).

Furthermore, the following carbobenzyloxy-(Z)-peptidyl-diazomethylketone inhibitors were tested (all at a final concentration of 0.1 mM during preincubation with barium-activating protease): Z-Leu-Leu-Tyr-$CHN_2$, Z-Val-Val-Tyr-$CHN_2$, Z-Phe-Ala-$CHN_2$, Z-Phe(I)-Ala-$CHN_2$, Z-Tyr-Ala-$CHN_2$ and Z-Phe-Phe-$CHN_2$.

After the preincubaticon, 100 μl aliquots of the enzyme inhibitor mixtures were added to 50 μl of purified vWF solution, and the mixtures were dialyzed against 1 M urea, 5 mM Tris-HCl, at pH 7.4 for 24 hours at 37° C. The degradation of vWF was assayed with SDS agarose electrophoresis and immunoblotting (cf, FIG. 9(panel A).

The chelating agents EDTA and ESTA could inhibit the barium-preincubated protease completely, whereas with citrate only a partial inhibition could be attained. A 15-minute preincubation with sulfhydryl enzyme inhibitors IAA and NEM did not result in protease inhibition. There was also no inhibition of the protease according to the invention by serine protease inhibitors DFP, PMSF and aprotinin, or by serine/sulfhydryl protease inhibitors TLCK, TPCK and leupeptin.

In further experiments in which the same inhibitors were also incorporated into the dialysis solution, the same results were obtained, with one exception: with NEM a partial protease inhibition could be achieved.

Thus, it appears that the protease is very slowly inhibited by NEM, albeit not by IAA.

Among the peptidyl diazomethylketons inhibitors tested, only Z-Phe-Phe-$CH_2$ and Z-Val-Val-Tyr-$CHN_2$ impaired the proteolytic degradation of vWF (cf. FIG. 9 (panel B).

Polypeptide Subunits of Degraded vWF and of other Proteins

Purified vWF (50 μl) was mixed with various dilutions of the protease (100 μl) which had been preincubated with 10 mM barium chloride for 5 minutes at 37° C., and the mixtures were dialyzed against 1 M urea, 5 mM Tris-HCl, pH 8.0, for 24 hours at 37° C. The resulting digests were subjected to SDS-PACE After having been reduced with DTT. Immunodetection of the reduced vWF fragments war performed by using the APAAP kit.

Figure 10:
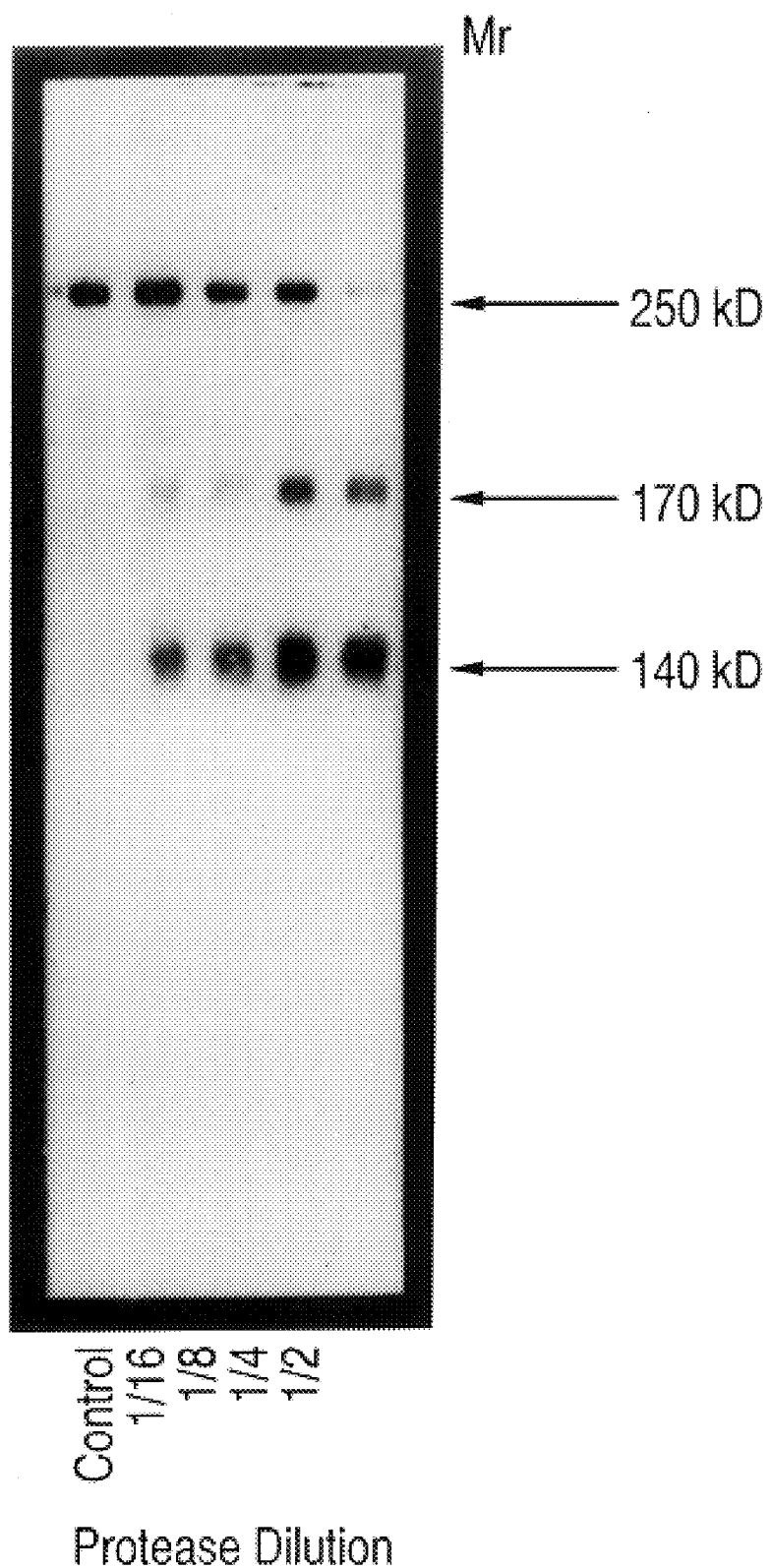
FIG. 10 shows an SDS-PAGE of the vWF degradation products.

The degradation of the intact vWF subunit was accompanied by the appearance of increasing amounts of two fragments with a molecular weight of 170 and 140 kD, respectively, as shown by immunoblots of reduced SDS-PACE (cf. FIG. 10).

In parallel experiments, three other proteins were incubated with the purified protease, i.e. 50 μl solutions each of human fibrinogen (0.4 mg/ml), BSA (0.2 mg/ml) or calf skin collagen (0.4 mg/ml) each incubated with 100 μl of the undiluted protease that had been preincubated with barium ions, and the incubation mixtures were dialyzed against 1 M urea, 5 mM Tris-HCl, pH 8.0, for 24 hours at 37° C. Furthermore, citrated human normal plasma (dilution 1:100) was dialyzed together with the protease preparation according to the invention. In control experiments, the protease was replaced by 0.15 M sodium chloride/0.01 M Tris-HCl, pH 7.4. After the dialysis, the proteins were reduced with DTT and applied to an SDS-PAGE. Coomassie-Blue staining was used for the detection of the polypeptide chains.

It was shown that under vWF degrading conditions, no degradation of human fibrinogen, BSA or calf skin collagen could be observed with the protease preparation according to the invention (cf FIG. 11). The reduced SDS-PAGE showed unchanged subunit chains of these proteins which had been used as potential substrates, indicating that the protease of the invention has a high specificity for vWF.

Amino Acid Analysis and Amino Acid Sequence of vWF and its Degradation Products

All three electrophoretic bands shown in FIG. 10, i.e. the 250, 170 and 140 kD bands, were transferred onto PVDF membrane and subjected to analysis of amino acid composition and amino acid sequence. The results are shown in Table 2 and demonstrate good agreement between the amino acid composition of these three polypeptide bands and the theoretical values calculated for the intact vWF subunit, C-terminal fragment 843–2050, and N-terminal fragment 1–842, respectively; cf. EP-0 197 592 in this respect. The N-terminal amino acid sequence of the 250- and 140-kD bands was Ser-Lou-Ser-X-Arg; this sequence agrees with the N-terminal sequence of the intact vWF subunit. Analysis of the larger degradation product with the molecular mass 170 kD yielded an N-terminal Sequence of Met-Val-Thr-Gly-Asn corresponding to amino acid residues 843–847 in the intact vWF subunit. These data indicate that the purified protease cleaves the peptide bond 842Tyr-843Met.

showed an increase already after a short incubation. The degradation could not be prevented by the addition of the protease inhibitors (aprotinin, FIG. 13 (panel B)), and PPACK, FIG. 13 (panel C)); however, it could be slowed down. If a preparation of the highest molecular weight vWF multimers (cF. FIG. 14 (panel A)) produced for this purpose was used instead of the cryoprecipitate [laboratory preparation 10 U (Ag)/ml in 20 mm TBS buffer, pH 8.3], a clear shift towards lower molecular weight multimers with an increase in the satellite bands could be detected with the vWF protease according to the invention. Overnight digestion with plasmin completely degraded both plasmatic vWF

TABLE 2

| Amino Acid | $M_t \sim 250$ kD | vWf 1-2050 | $M_t \sim 170$ kD | vWF 843-2050 | $M_t \sim 140$ kD | vWF 3-842 |
|---|---|---|---|---|---|---|
| Asp + Asn | 173 | 187 | 102 | 108 | 77 | 79 |
| Thr | 118 | 116 | 70 | 78 | 39 | 38 |
| Ser | 131 | 141 | 78 | 80 | 55 | 61 |
| Glu + Gln | 249 | 237 | 152 | 139 | 104 | 98 |
| Pro | 139 | 136 | 85 | 86 | 54 | 50 |
| Gly | 152 | 137 | 117 | 86 | 76 | 51 |
| Ala | 110 | 104 | 67 | 60 | 50 | 44 |
| Val | 171 | 184 | 87 | 103 | 66 | 81 |
| Ile | 75 | 78 | 41 | 44 | 30 | 34 |
| Leu | 163 | 156 | 86 | 83 | 73 | 73 |
| Tyr | 48 | 49 | 18 | 22 | 21 | 27 |
| Phe | 58 | 56 | 33 | 32 | 25 | 24 |
| His | 53 | 52 | 28 | 31 | 19 | 21 |
| Lys | 87 | 88 | 45 | 47 | 39 | 41 |
| Arg | 95 | 101 | 49 | 58 | 38 | 43 |

Proteolytic Fragmentation of Recombinant vWF

Recombinant vWF factor (r-vWF), produced according to FEBS-Letters 375, 259–262 (1995) with a concentration of 104 U (Ag)/ml in 20 mM TBS buffer, pH 8.3, was incubated as described above with the vWF protease preparation according to the invention. A loss of the highest multimers was already found after 3 h, with a formation of satellite bands similar to those of plasmatic vWF. After 20 hours, oligomers and multimers could no longer be detected (cf. FIG. 12 (panel A).

After copper chelate affinity chromatography, the preparation prepared according to the invention with the vWF-specific protease still exhibited a clearly measurable plasmin activity (0.2 U/ml; determined by preheating 50 μl sample or standard (human plasmin from Chromogenics, with 19.3 U/ml in 20 mM TBS buffer, pH 8.3) for one minute at 37° C. and admixing with 200 μl chromogenic substrate PL1 from Immuno AG (D-cyclohexylglycyl-L-alanyl-L-arginine-p-nitroanlide, 1 mM in TBS buffer, pH 8.3), and subsequently measuring the kinetics of the liberation of p-nitroaniline photometrically at 405 nm at 37° C.). Thus, it was necessary to exclude the possibility that the protease preparation might effect a degradation of the von Willebrand factor multimers due to plasmin present in the preparation rather than as a result of the vWF-specific protease.

FIG. 12 (panels B and C) show that recombinant vWF is degraded identically when incubated with the protease according to the invention in the presence of a plasmin inhibitor (aprotinin) and a protease inhibitor with less specificity for plasmin, such as PPACK. The concentration of aprotinin and PPACK was chosen such that no protease activity could be detected with a chromogenic substrate of plasmin.

When incubating cryoprecipitate with vWF protease (FIG. 13 (panel A)), a loss of multimers could be observed over time just as with recombinant vWF. The satellite bands and recombinant vWF (cf. FIG. 14 (panels B and D)). In this experiment, the degradation products of the recombinant vWF with the protease according to the invention were the satellite bands developed and the central bands. Actually all bands were very similar to plasmatic vWF (FIG. 14 (panel C)).

Incubation of r-vWF with plasmin (cf. FIG. 15; plasmin being diluted to 0.2 U/ml in 20 mM TBS buffer, pH 8.3 and admixed 1:1 with the respective r-vWF preparation and incubated at 37° C.) at lower concentration, based on the substrate present, showed a successive degradation of the multimers over 29 h (cf. FIG. 15 (panel A)) in the kinetic examination. A control preparation without protease demonstrates the otherwise found stability of the r-vWF in solution (CF. FIG. 15 (panel C)). When reducing the plasmin concentration to 1:10, r-vWF was degraded more slowly (FIG. 15 (panel B)); this could be prevented by the addition of aprotinin (cf. FIG. 16 (panel B)) and PPACK (cf. FIG. 16 (panel C)). The multimers showed no change over time (about 20 hours), in contrast to the situation after treatment without inhibitor (cf. FIG. 16 (panel A)).

The control experiment with cryoprecipitate (FIG. 17) with incubation for more than 8 hours again shows a reduction of the high multimers which could be prevented by adding aprotinin or PPACK.

Figures 18A, 18B:
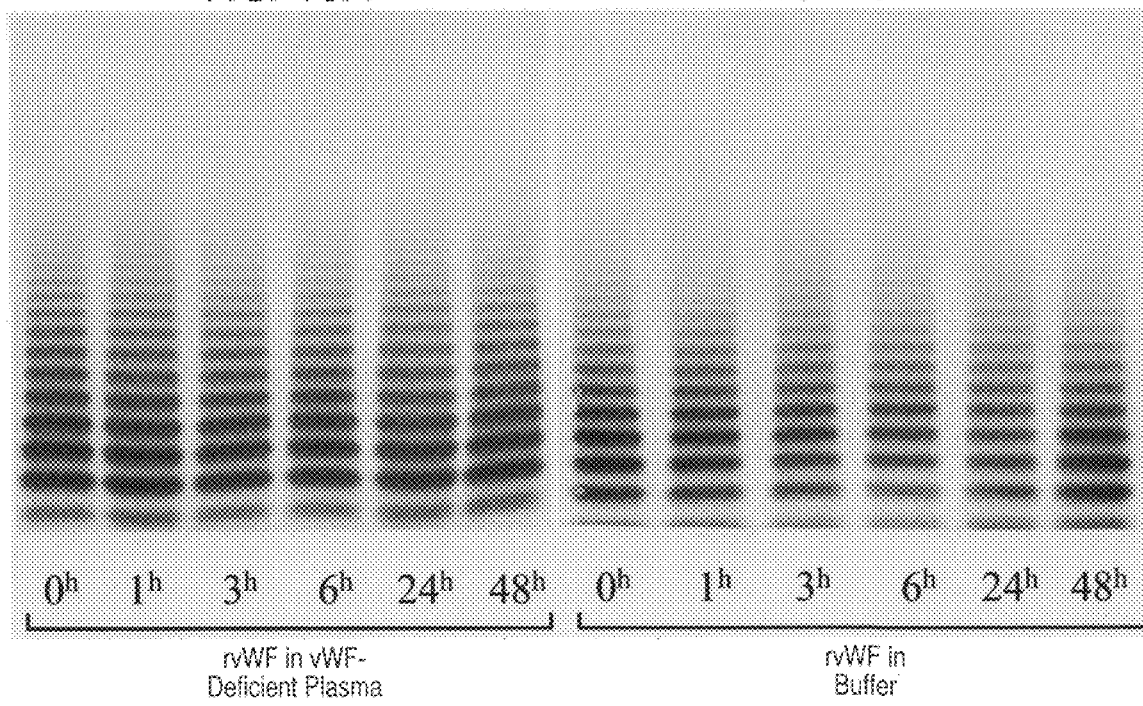
FIG. 18 (panels A and B) shows the incubation of r-vWF in vWF-deficient human plasma.

Further tests investigated whether a proteolytic degradation of r-vWF took place during incubation with human plasma (cf. FIG. 18). For this, the r-vWF preparation was mixed with equal volumes of a vWF-deficient plasma (cf. FIG. 18 (panel A)) and incubated for 48 hours, samples being taken at various times. No change of the r-vWF over time could be detected. A control preparation allowed to stand for an equal length of time at 37° C. in buffer media also showed no change of structure (cf. FIG. 18 (panel B)).

Analysis of the r-vWF and its proteolytic degradation products was performed on 1% and 2% agarose gels, also according to the method of Ruggeri et al. (Blood 57 (1981), 1140–1143). The vWF multimers were made visible by immunoenzymatic staining according to Aihara et al. (Thromb. Haemostas. 55 (1986), 263–267). A rabbit-anti-von Willebrand factor-antiserum (from Dakopatts, Glostrup, Denmark) was used as the primary antibody, and an alkaline phosphatase-conjugated, affinity-purified goat-anti-rabbit IgG H+L-antibody (from Axell Accurate Chemical and Scientific Corp, Westburg, N.Y.) served as the secondary antibody. Staining of the protein bands was effected by means of the nitroblue tetrazolium/bromochloro-indolyl-phosphate substrate system.

It is to be understood that the description, specific examples and data, while indicating preferred embodiments, are given by way of illustration and exemplification and are not intended to limit the present invention. Various changes and modifications within the present invention will become apparent to the skilled artisan from the discussion, disclosure and data contained herein.

What is claimed is:

1. A purified multimerase that is involved in proteolysis and converts singlet von Willebrand Factor (vWF) to satellite vWF and is active in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-CHN$_2$), wherein the multimerase is purified to be at least 1000-fold enriched for the multimerase as compared to plasma.

2. A purified multimerase according to claim 1, wherein the purified multimerase cleaves vWF between amino acids 842 Tyr and 843 Met.

3. A purified multimerase according to claim 1, wherein the multimerase is purified to be least 10,000-fold enriched for the multimerase as compared to plasma.

4. A purified multimerase according to claim 1, wherein the multimerase has a specific activity of at least 10 U/mg protein while in the presence of a serine protease inhibitor.

5. A purified multimerase according to claim 1, wherein the multimerase is active in the presence of bivalent metal ions.

6. A purified multimerase according to claim 5, wherein the bivalent metal ions are alkaline earth ions.

7. A purified multimerase according to claim 1, wherein the level of the activity of the multimerase can be increased by any one of shearing forces, reduced ionic strength and chaotropic agents.

8. A purified multimerase according to claim 7, wherein the level of the activity of the multimerase is increased by reducing ionic strength below physiologic levels.

9. A purified multimerase according to claim 1, wherein the multimerase is effective on denatured vWF and conformationally modified vWF.

10. A method of preparing a purified multimerase that is involved in proteolysis and converts singlet von Willebrand Factor (vWF) to satellite vWF and is active in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-CHN$_2$), comprising subjecting at least one of plasma, a plasma fraction, serum and serum fraction to a chromatographic process to obtain isolated fractions, and recovering isolated fractions that exhibit a vWF inactivating activity in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-CHN$_2$), wherein the fractions are at least 1000-fold enriched for the multimerase as compared to plasma.

11. A method according to claim 10, wherein the chromatographic process is selected from the group consisting of ion exchange chromatography, affinity chromatography and gel filtration.

12. A method according to claim 10, wherein the recovered isolated fractions are at least 10,000-fold enriched for the multimerase as compared to plasma.

13. A preparation comprising a purified multimerase that is involved in proteolysis and converts singlet von Willebrand Factor (vWF) to satellite vWF and is active in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-CHN$_2$), wherein the preparation is at least 1000-fold enriched for the multimerase as compared to plasma.

14. A preparation according to claim 13, wherein the multimerase is at least 1000 fold purer than the multimerase in plasma.

15. A preparation according to claim 14, wherein the preparation is at least 10,000-fold enriched for the multimerase as compared to plasma.

16. A preparation according to claim 13, wherein the multimerase has a specific activity of at least 10 U/mg protein while in the presence of a serine protease inhibitor.

17. A purified multimerase according to claim 1, wherein the pH range for optimum activity of the multimerase is between pH 7 to pH 10.

18. A purified multimerase that is involved in proteolysis and converts singlet von Willebrand Factor (vWF) to satellite vWF and is active in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-CHN$_2$), wherein the multimerase has been subjected to a purification process to remove impurities, and is at least 1000-fold enriched for the multimerase as compared to plasma.

19. A purified multimerase according to claim 18, wherein the purified multimerase cleaves vWF between amino acids 842 Tyr and 843 Met.

20. A purified multimerase according to claim 18, wherein the multimerase is at least 10,000-fold enriched for the multimerase as compared to plasma.

21. A purified multimerase according to claim 18, wherein the multimerase has a specific activity of at least 10 U/mg protein while in the presence of a serine protease inhibitor.

22. A method of preparing a multimerase-containing preparation, wherein the multimerase is involved in proteolysis and converts singlet von Willebrand Factor (vWF) to satellite vWF and is active in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-CHN$_2$), comprising subjecting at least one of plasma, a plasma fraction, serum and serum fraction to a purification process to remove contaminants and to obtain isolated fractions, and recovering isolated fractions that exhibit a vWF inactivating activity in the presence of serine protease inhibitor diisopropyl fluorophosphate (DFP) and calpain protease inhibitor carbobenzyloxy (Z) peptidyl diazomethylketone inhibitor (Z-Leu-Leu-Tyr-$CHN_2$), to obtain a preparation that is at least 1000-fold enriched for the multimerase as compared to plasma.

23. A purified multimerase according to claim 1, wherein multimerase is obtained by subjecting one of plasma, a plasma fraction, serum and serum fraction to a chromatographic process, and the mutimerase activity elutes or migrates with molecules having a molecular weight greater than 200 kD.

24. A preparation according to claim 13, wherein multimerase is obtained by subjecting one of plasma, a plasma fraction, serum and serum fraction to a chromatographic process, and the mutimerase activity elutes or migrates with molecules having a molecular weight greater than 200 kD.

25. A purified multimerase according to claim 18, wherein multimerase is obtained by subjecting one of plasma, a plasma fraction, serum and serum fraction to a chromatographic process, and the mutimerase activity elutes or migrates with molecules having a molecular weight greater than 200 kD.

26. A method according to claim 22, wherein the preparation is at least 10,000-fold enriched for the multimerase as compared to plasma.

27. A method according to claim 22, wherein the preparation has a specific activity for the multimerase of at least 10 U/mg protein while in the presence of a serine protease inhibitor.

28. A method according to claim 22, wherein the multimerase is active in the presence of bivalent metal ions.

29. A method according to claim 28, wherein the bivalent metal ions are alkaline earth ions.

30. A method according to claim 22, wherein the level of the activity of the multimerase can be increased by any one of shearing forces, reduced ionic strength and chaotropic agents.

31. A method according to claim 22, wherein the level of the activity of the multimerase is increased by reducing ionic strength below physiologic levels.

32. A method according to claim 22, wherein the multimerase is effective on denatured vWF and conformationally modified vWF.

* * * * *